US010598655B2

(12) United States Patent
Nutman et al.

(10) Patent No.: US 10,598,655 B2
(45) Date of Patent: Mar. 24, 2020

(54) **COMPOSITIONS AND METHODS FOR DETECTING *LOA LOA***

(71) Applicant: The United States of America, as represented by the Secretary, Department of Health and Human Services, Bethesda, MD (US)

(72) Inventors: Thomas B. Nutman, Chevy Chase, MD (US); Sasisekhar Bennuru, Rockville, MD (US); Papa Makhktar Drame, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 61 days.

(21) Appl. No.: 15/569,507

(22) PCT Filed: Apr. 28, 2016

(86) PCT No.: PCT/US2016/029673
§ 371 (c)(1),
(2) Date: Oct. 26, 2017

(87) PCT Pub. No.: WO2016/176395
PCT Pub. Date: Nov. 3, 2016

(65) Prior Publication Data

US 2018/0209967 A1 Jul. 26, 2018

Related U.S. Application Data

(60) Provisional application No. 62/153,654, filed on Apr. 28, 2015.

(51) Int. Cl.

| | |
|---|---|
| ***A61K 39/00*** | (2006.01) |
| ***A61K 39/395*** | (2006.01) |
| ***C12Q 1/00*** | (2006.01) |
| ***G01N 33/53*** | (2006.01) |
| ***C07K 16/18*** | (2006.01) |
| ***C07K 14/435*** | (2006.01) |

(52) U.S. Cl.
CPC ..... *G01N 33/5308* (2013.01); *C07K 14/4354* (2013.01); *C07K 16/18* (2013.01); *G01N 2333/4353* (2013.01); *G01N 2469/20* (2013.01)

(58) Field of Classification Search
CPC . A61K 39/00; A61K 39/395; A61K 39/39575
USPC ......... 424/130.1, 139.1, 151.1, 184.1, 185.1; 435/4, 7.1, 7.2
See application file for complete search history.

(56) References Cited

FOREIGN PATENT DOCUMENTS

WO WO 02/38600 A2 5/2002

OTHER PUBLICATIONS

Fernandez0Soto, P., et al. PloS One, vol. 9, No. 4, article e94664, 2014.*
Akue et al., "Markers of Loa loa infection in permanent residents of a loiasis endemic area of Gabon," *Trans. R. Soc. Trop. Med. Hyg.*, 90 (2), 115-118 (1996).
Burbelo et al., "A simplified immunoprecipitation method for quantitatively measuring antibody responses in clinical sera samples by using mammalian-produced Renilla luciferase-antigen fusion proteins." *BMC Bietechnol.*, 5, 22 (2005).
Burbelo et al., "Antibody profiling by Luciferase Immunoprecipitation Systems (LIPS)," *J. Vis. Exp.*, (32) doi:10.3791/1549 (2009).
Burbelo et al., "Luciferase immunoprecipitation systems for measuring antibodies in autoimmune and infectious diseases," *Transl. Res.*, 165 (2), 325-335 (2015) Author Manuscript.
Burbelo et al., "Rapid, novel, specific, high-throughput assay for diagnosis of Loa loa infection," *J. Clin. Microblol.*, 46 (7), 2298-2304 (2008).
Desjardins et al., "Genomics of Loa loa, a Wolbachia-free filarial parasite of humans," *Nat. Genet.*, 45 (5), 495-500 (2013).
Dickerson et al., "A technique for microfilarial detection in preserved blood using nuclepore filters," *J. Parasitol.*, 76 (6), 829-833 (1990).
Drame et al., "Identification and Validation of Loa loa Microfilaria-Specific Biomarkers: a Rational Design Approach Using Proteomics and Novel Immunoassays," *MBio.*, 7 (1), e02132-15, pp. 1-8 (2016).
Drame et al., "Loop-mediated isothermal amplification for rapid and semiquantitative detection of Loa loa infection," *J. Clin. Microbiol.*, 52 (6), 2071-2077 (2014).
Fink et al., "Rapid molecular assays for specific detection and quantitation of Loa loa microfilaremia," *Plos. Negl. Trop. Dis.*, 5 (8), e1299, 1-8 (2011).
Henrard et al., "Detection of p24 antifgen with and without immune complex dissociation for longitudinal monitoring of human immunodeficiency virus type 1 infection," *J. Clin. Microbiol.*, 33 (1), 72-75 (1995).
International Preliminary Report on Patentability, Application No. PCT/US2016/029673, dated Oct. 31, 2017.
International Search Report, Application No. PCT/US2016/029673, dated Jul. 20, 2016.
Klion et al., "Serum immunoglobulin G4 antibodies to the recombinant antigen, LI-SXP-1, are highly specific for Loa loa infection," *J. Infect. Dis.*, 187 (1), 128-133 (2003).
Moody et al., "Methods for the detection of blood parasites," *Clin. Lab. Haematol.*, 22 (4), 189-201 (2000).

(Continued)

*Primary Examiner* — Rodney P Swartz
(74) *Attorney, Agent, or Firm* — Leydig, Voit & Mayer, Ltd.

(57) ABSTRACT

Disclosed are methods of detecting the presence of *Loa loa* in a biological sample using one or more antigens, each having a different amino acid sequence selected from the group consisting of SEQ ID NOs: 1-20. Related compositions, specific binding partners, and test kits are also disclosed.

28 Claims, 9 Drawing Sheets

Figure 1:
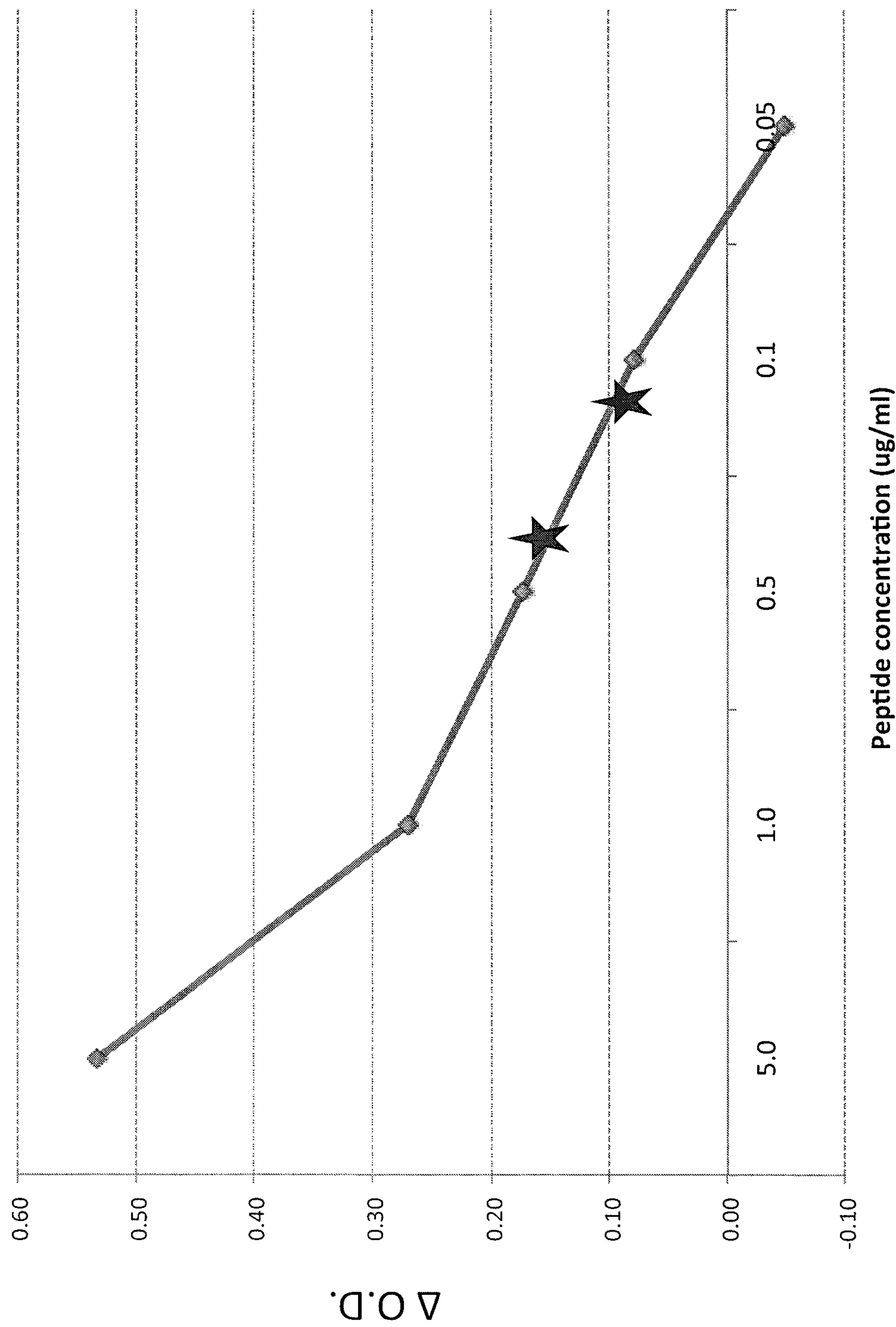

Specification includes a Sequence Listing.

(56) References Cited

OTHER PUBLICATIONS

Nagaraj et al., "Quantitative analysis of the intra- and inter-individual variablility of the normal urinary proteome," *J. Proteome Res.*, 10 (2), 637-645 (2011).

Suarez-Pantaleon et al., "Production of polyclonal antibodies directed to recombinant methionyl bovine somatotropin." *Anal. Chim. Acta.*, 761, 186-193 (2013).

Toure et al., "Detection of Loa loa-specific DNA in blood from occult-infected individuals," *Exp. Parasitol.*, 86 (3), 163-170 (1997).

Walker-Deemin et al., "Detection of circulating antigens in Gabonese patients with Loa loa filariasis," *Trop. Med. Int. Health*, 1 (6), 772-778 (1996).

Written Opinion of the International Searching Authority, Application No. PCT/US2016/029673, dated Jul. 20, 2016.

* cited by examiner

LOAG_17808
Estimated protein conc (ng/mL)
270
240
210
180
150
120
90
60
30
0
L. loa
W. bancrofti
O. volvulus
Controls LOAG_16297
Estimated protein conc (ng/mL)
150
120
90
60
30
0
L. loa
W. bancrofti
O. volvulus
Controls

LOAG_17808
r=0.61; p=0.0002

Count of microfilaria (x10$^3$/ml)

Estimated protein conc (ng/ml)

SEQUENCE LISTING

```
<160> NUMBER OF SEQ ID NOS: 20

<210> SEQ ID NO 1
<211> LENGTH: 911
<212> TYPE: PRT
<213> ORGANISM: Loa loa

<400> SEQUENCE: 1

Met Asp Pro Thr Ser Leu Gly Phe Val Ala Val Ile Ala Val Leu Ile
1               5                   10                  15

Ile Ile Ile Ser Ile Ile Val Phe Lys Met Tyr Pro Lys Glu Thr Asp
            20                  25                  30

Phe Glu Lys Ala Tyr Gly Glu Asn Ala Leu Arg Leu Leu Thr Glu Asp
        35                  40                  45

Arg Ala Asn Lys Thr Lys Ser Ala Lys Asn Lys Asn Lys Gly Lys Asn
    50                  55                  60

Gly Asp Lys Lys Arg Asp Leu Gly Ala Glu Glu Lys Gln Asn Arg Asn
65                  70                  75                  80

Glu Lys Pro Ala Asn Gly Asp Leu His Tyr Ile Pro Leu Ser Thr Asn
                85                  90                  95

Gly His Cys Gly Thr Glu Gly Trp Asn Gly Thr Asn Asn Gly Glu Val
            100                 105                 110

Asp Gly Lys Pro Asn His Lys Lys Leu Lys Gly Lys Gln Leu Val Ala
        115                 120                 125

Glu Ile Met Gln His Thr Glu Ser Ala Lys Asp Glu Lys Val Ala Val
    130                 135                 140

Ala Lys Asn Met Glu Gly Leu Ser Gly Gln Arg Val Val Ala Glu Lys
145                 150                 155                 160

Leu Asn Asp Glu Pro Glu Val Val Pro Ser Ala Arg Ile Leu His Asp
                165                 170                 175

Glu Asn Lys Gly Ser Asp Val Gly Glu Arg Lys Gly Lys Lys Lys Asn
            180                 185                 190

Arg Val Arg Arg Asn Lys Glu Tyr Leu Arg Glu Ile Thr Lys Gly Glu
        195                 200                 205

Val Arg Val Thr Glu Glu Ile Val Pro Ala Met Asp Val Ile Pro Pro
    210                 215                 220

Leu Glu Ser Glu Gln Glu Lys Leu Glu Lys Pro Lys Ser Lys Lys Pro
225                 230                 235                 240

Asn Pro Leu Lys Asp Ile Asn Ala Asn Lys Leu Gln Ala Arg Leu Asn
                245                 250                 255

Ala Ile Ala Glu Leu Glu Pro Glu Tyr Val Thr Phe Leu Thr Asn Tyr
            260                 265                 270

Ile Asn Asn Val Asn Thr Gln Arg Ala Lys Leu Asp Gly Glu Ile Ala
        275                 280                 285

Leu Met Arg Lys Gln Ile Ala Asp Lys Asp Arg Leu Val Leu Tyr Cys
    290                 295                 300
```

-continued

```
Thr Asn Lys Leu Thr Thr Ala Glu Gln Lys Asp Ser Glu Ile Ala Met
305                 310                 315                 320

Leu Gln Lys Thr Leu Ala Glu Glu Lys Arg Lys Tyr Lys Met Phe Glu
                325                 330                 335

Gln Thr Val Cys Ala Gln Leu Ser Asn Asn Ala Gln Glu Lys Ser Tyr
            340                 345                 350

Leu Gln Arg Lys Tyr Asp Gln Leu Gln Gly Glu Phe Gly Ala Leu Arg
        355                 360                 365

Glu Glu Met Lys Lys Ala Gln Ser Val Ile His Ser Ala Pro Pro Pro
    370                 375                 380

Ile Asp Thr Lys Pro Tyr Gln Gln Gln Ile Asp Arg Leu Lys Ala Glu
385                 390                 395                 400

Leu Thr Ser Ser Lys Asn Arg Cys Ser Gln Gln Glu Leu Glu Leu Asn
                405                 410                 415

Gln Arg Leu Gln Ala Leu Gln Gln Ile Arg Lys Glu Leu Gln Asn Gln
            420                 425                 430

Asp Cys Gln Ile Glu His Leu Ser Lys Thr Asn Ala Leu Leu Glu Lys
        435                 440                 445

Arg Leu Gln Glu Val Glu Gly Asn Ala Lys Ala Glu Arg Asp Thr Leu
    450                 455                 460

Glu Lys Lys Leu Gln Asn Thr Met Lys Val Ala Glu Glu Leu Ser Val
465                 470                 475                 480

Val Thr Ser Glu Ile Arg Asp Glu Met Leu Gln His Arg Gly Asn Ala
                485                 490                 495

Glu Thr Ala Val Gln Glu Arg Glu Lys His Cys Glu Gln Ile His Ile
            500                 505                 510

Leu Asn Ala Gln Leu Met Asp Ala Asn Arg Glu Arg Val Arg Tyr Leu
        515                 520                 525

Asn Asp Cys Ala Val Tyr Ser Lys Lys Leu Thr Glu Met Glu Thr Ala
    530                 535                 540

Asn Ala Glu Leu Ser Glu Gln Leu Lys Val Leu Gln Asn Thr Ser Ala
545                 550                 555                 560

Thr Ser Asp Ala Asn Cys Ser Glu Leu Thr Lys Glu Val Glu Lys Tyr
                565                 570                 575

Arg Lys Gln Leu Val Asp Ile Met Glu Ala His Asp Lys Asp Val Ala
            580                 585                 590

Lys Leu Lys Asn Gln Leu Glu Cys Val Gln Glu Glu Lys Glu Asn Ile
        595                 600                 605

Ser Lys Glu Ala Val Glu Val Ala Lys Cys Arg Lys Glu Leu Asn Glu
    610                 615                 620

Phe Lys Ile Glu Tyr Asp Lys Lys Leu Asn Arg Ile Val Ser Leu Glu
625                 630                 635                 640

Glu Glu Val Ala Lys Tyr Lys Glu Ile Glu Ile Lys Arg Lys Thr Met
                645                 650                 655

Val Pro Ser Pro Asp Asn Asn Gly Thr Asp Val Asn Glu Lys Met Met
            660                 665                 670

Lys His Arg Val Gln Ser Ala Ala Lys Asp Asp Val Val Cys Gly Asn
        675                 680                 685

Asn Val Asn Leu Glu Val Thr Arg Leu Lys Arg Gln Asn Glu Glu Leu
    690                 695                 700

Arg Lys Ala Asn Tyr Lys Val Val Glu Ile Ser Gln Gln Gln Glu Ala
705                 710                 715                 720
```

```
Ile Phe Lys Lys His Leu Glu Glu Leu Lys Lys Lys Tyr Glu Val Glu
                725                 730                 735

Leu Gln Gln Tyr Cys Cys Lys Val Phe Glu Thr Leu Cys Ala Ile Ala
            740                 745                 750

Pro Pro Asn Ile Lys Leu Pro Asn Leu Ser Asn Ile Tyr Asp Met Asp
        755                 760                 765

Gln Phe Cys Lys Trp Leu Lys Asn Val Glu Asn Val Val Gln Lys Ser
    770                 775                 780

Glu Asn Val Gln Gln Phe Asn Lys Asn Glu Asp Asp Glu Ser Gly Asn
785                 790                 795                 800

Lys Val Asp Leu Thr Lys Val Ala Glu Leu Glu Ala Ser Asn Arg Arg
                805                 810                 815

Tyr Arg Ala Ala Leu Ala Ser Leu Ser Ser His Ile Asp Thr Ile Glu
            820                 825                 830

Gln Glu Ala Ile Ser Lys Glu Lys Ile Tyr Leu Ser Glu Ile Ser Cys
        835                 840                 845

Leu Arg His Glu Val Asn Glu Gln Leu Lys Lys Arg Leu Glu Asn Glu
    850                 855                 860

His Lys Arg Lys Leu Glu Leu Ile Ser Gln Ala Ser Lys Leu Cys Glu
865                 870                 875                 880

Ile Ile Asn Gly Ser Gln Lys Tyr Gly Asn Gly Gly Ala Glu Pro Thr
                885                 890                 895

Val Lys Ser Glu Asn Ala Tyr Asp Phe Gly Gly Ala Asn His Ile
            900                 905                 910


<210> SEQ ID NO 2
<211> LENGTH: 893
<212> TYPE: PRT
<213> ORGANISM: Loa loa

<400> SEQUENCE: 2

Met Ser Tyr Asn Leu Cys Lys Ile Lys Asn Leu Asp Asn Ala Glu Arg
1               5                   10                  15

Gln Ile Arg Arg Leu Glu Glu Arg Leu Arg Ala Ala Asp Leu Glu Lys
            20                  25                  30

Ala Ala Ile Glu Lys Ala Arg Lys Phe Leu Glu Glu Glu Ile Asn Lys
        35                  40                  45

Leu His Gln Gln Tyr Gln Lys Ala Thr Ala Glu Glu Glu Arg Lys Ala
    50                  55                  60

Arg Asp Lys Gln His Glu Ile Asn Leu Gly Leu Glu Glu Glu Tyr Lys
65                  70                  75                  80

Asn Arg Ile Asn Glu Leu Lys Ser Arg Ile Glu Thr Ile Gln Arg Asp
                85                  90                  95

Asn Thr Lys Leu Lys Thr Glu Leu Asn Thr Met Arg Asp Lys Tyr Arg
            100                 105                 110

Asp Thr Glu Asn Glu Tyr Asn Ile Thr Leu Arg Lys Leu Glu Glu Lys
        115                 120                 125

Asp Ala Ala Leu Arg His Leu Asp Glu Thr Lys Arg Gln Phe Thr Asn
    130                 135                 140

Glu Leu Asp Gln Gln Arg Thr Arg Tyr Asp Thr Leu Asn Ser Glu Phe
145                 150                 155                 160

Asp Arg Leu Asn Asn Glu Tyr Glu Asn Ala Asn Lys Thr Val Val Thr
                165                 170                 175

Leu Glu Gln Thr Val Arg Glu Ile Lys Gln Gln Arg Asp Glu Tyr Gly
            180                 185                 190
```

```
Lys Gln Lys Asp Glu Leu Ser Arg Gln Met Phe Asp Leu Lys His Gln
        195                 200                 205

Leu Glu Asn Glu Lys Ala Ala Arg Glu Glu Ala Glu Lys Thr Thr Ser
    210                 215                 220

Arg Leu Thr Gln Glu Ile Glu Lys Phe Lys Leu Gln Ile Thr Asp Tyr
225                 230                 235                 240

Glu Asn Gln Leu Ser Met Leu Arg Arg His Asn Asp Glu Leu Asp Thr
                245                 250                 255

Gln Ile Lys Ser Gly Gln Ala Lys Ile Thr Ala Ile Glu Asn Asp Leu
            260                 265                 270

Ile Thr Ser Gln Lys Glu Thr Val Arg Leu Asn Glu Leu Asn Ser Arg
        275                 280                 285

Leu Gln Arg Glu Lys Gln Asp Ala Ile Asn Gln Lys Leu Lys Ala Glu
    290                 295                 300

Ser Asp Ala Glu Val Trp Lys Glu Gln Ile Arg Arg Leu Glu Leu Glu
305                 310                 315                 320

Ile Glu Lys Leu Lys Ile Glu Asn Arg Thr Ile Thr Glu Gln Glu Glu
                325                 330                 335

Lys Thr Arg Asp Ala Leu Thr Lys Glu Thr Asn Arg Ala His Leu Leu
            340                 345                 350

Gln Lys Glu Leu Glu Glu Thr Lys Ala Glu Ile Glu Glu Leu Glu Lys
        355                 360                 365

Lys Ile Lys Arg Leu Glu Gln Glu Ile Glu Ser Ser Ser Arg Gly Thr
    370                 375                 380

Arg Lys Asp Glu Ser Glu Glu Thr Asp Lys Ile Ser Leu Gly Pro Ser
385                 390                 395                 400

Gly Pro Thr Val Tyr Asp Thr Glu Ile His Glu Ile Arg Ile Arg Glu
                405                 410                 415

Val Asn Asp Lys Trp Lys Leu Glu Phe Asp Lys Ile Leu Gly Glu Lys
            420                 425                 430

Asp Glu Leu Glu Arg Arg Ile Arg Asp Leu Glu Asp Gln Ile Thr Gln
        435                 440                 445

Lys Asn Arg Glu Phe Glu Arg Gln Glu Thr Glu Ile Ala Glu Leu Lys
    450                 455                 460

Arg Lys His Gln Glu Glu Ile Asp Arg Leu Arg Ser Glu Ile Ser Gln
465                 470                 475                 480

Leu His Asp Lys His Gln Asn Asp Leu Asp Asp Glu Lys Glu Gln Tyr
                485                 490                 495

Asn Lys Asn Leu Glu Ser Ile Lys Tyr Val Glu Asp Glu Leu Arg Asn
            500                 505                 510

Lys Leu Ala Glu Ala Glu Arg Lys Leu Ala Glu Ala Glu Asn Arg Glu
        515                 520                 525

Asn Gln Leu Glu Arg Glu Lys Val Glu Leu Lys Glu Lys Tyr Glu Gln
    530                 535                 540

Ala Leu Ala Gln Ile Gln Lys Leu Lys Asp Asp Leu Asp Asp Ala Arg
545                 550                 555                 560

Gln Glu Ala Glu Asn Glu Ile Gln Lys Trp Lys Thr Glu Val Tyr Ser
                565                 570                 575

Val Arg Ser Glu Leu Lys Ala Leu Glu Thr Ser Ser Asn Ala Leu Arg
            580                 585                 590

Thr Gln Leu Ala Ala Ala Asn Glu Arg Ala Glu Ser Leu Asn Lys Thr
        595                 600                 605
```

```
Val Asn Asp Gln Asn Gly Lys Ile Arg Glu Leu Asn Thr Gln Ile Arg
    610                 615                 620

Arg Leu Glu Glu Glu Ile Ser Asp Leu Lys Ser Ala Ala Val Thr Arg
625                 630                 635                 640

Glu Ser Asp Leu Glu Ser Ser Leu Ser Arg Leu Arg Ser Val Glu Asp
                645                 650                 655

Gln Tyr Ala Thr Leu Gln Ser Glu His Ala Lys Thr Arg Asn Glu Leu
            660                 665                 670

Glu Ile Leu Gln Arg Glu Tyr Asp Leu Leu Lys Ser Thr Asn Ile Asn
        675                 680                 685

Gln Glu Ser Glu Leu Glu Arg Leu Arg Asn Lys Ile Gln Gln Tyr Glu
    690                 695                 700

Val Thr Ile Lys Glu Gln Lys Asn Ala Leu Asp His Leu Lys Ala Glu
705                 710                 715                 720

Arg Glu Arg Leu Gln Asn Ile Tyr Arg Asp Lys Val Lys Gln Leu Asp
                725                 730                 735

His Leu Thr Gln Leu Val Gln Ser Phe Asp Val Lys Met Asn Lys Met
            740                 745                 750

Arg Gln Asn Leu Arg Asp Thr Ser Asp Lys Phe Val Ala Ala Glu Thr
        755                 760                 765

Glu Arg Asn Ala Leu Arg Ser Glu Val Thr Lys Leu Gln Gln Glu Leu
    770                 775                 780

Gln Phe Gly Lys Asp Gln Met Val Arg Arg Thr Asp Glu Tyr Gln Ser
785                 790                 795                 800

Ser Leu Glu Asp Leu Ala Asn Ala His Arg Ala Ala Glu Asp Gly Arg
                805                 810                 815

Leu Asn Ala Leu Gln Glu Leu Glu Ser Arg Lys Tyr Glu Leu Ala Asp
            820                 825                 830

Leu Lys Ser Arg Phe Glu Asn Thr Glu Gln Arg Leu Thr Ser Leu Gln
        835                 840                 845

His Asp Tyr Asn Lys Val Glu Asn Glu Arg Asp Ile Leu Ala Asp Ser
    850                 855                 860

Leu Lys Arg Phe Tyr Ser Val Thr Thr His Ala Val Thr Leu His Lys
865                 870                 875                 880

Val Lys Val Asn Tyr Leu Asn Glu Trp Ile Val Ile Glu
                885                 890


<210> SEQ ID NO 3
<211> LENGTH: 625
<212> TYPE: PRT
<213> ORGANISM: Loa loa

<400> SEQUENCE: 3

Met Gly Arg Lys Pro Val Arg Asn Ser Ala Pro Thr Ser Asp Leu Lys
1               5                   10                  15

Thr Gly Asp Val Val Trp Ala Pro Tyr Arg Arg Phe Pro Glu Trp Pro
            20                  25                  30

Ala Leu Val Arg Cys Val Tyr Pro Lys Lys Val Thr Tyr Thr Phe Leu
        35                  40                  45

Pro Ile Asn Glu Ser Ser Asn Leu Lys Ser Ser Ile Phe Ser Cys Pro
    50                  55                  60

Pro Gln Lys Leu Arg Leu Leu Thr Gly Asn Glu Ser Leu Pro Ala Gly
65                  70                  75                  80

Ala Lys Asn Asp Met Lys Glu Ala Tyr Lys Ala Ala Leu Glu Ile Leu
                85                  90                  95
```

```
Lys Lys Ser Gly Leu Leu Gly Ala Asp His Gln Met Ser Glu Glu Leu
            100                 105                 110

Ser Ala Phe Lys Ala Ser Glu Ile Asn Lys Gln Ser Val Leu Gly Asp
        115                 120                 125

Leu Val Lys Lys Thr Lys Lys Asp Ser Asp Ala Ala Ser Ser Gly Asp
    130                 135                 140

Thr Ala Ser Asn Ala Ser Ala Pro His Val Trp Gly Ile Gly Glu Val
145                 150                 155                 160

Val Trp Leu Ser Met Pro Asn His Ser Glu Trp Pro Val Val Ile Arg
                165                 170                 175

Glu Leu Lys Lys Lys Phe Ala Met Val Asp Ala Phe Pro Leu Lys Phe
            180                 185                 190

Asn Cys Lys Pro Glu Arg Tyr Pro Leu Ser Ala Cys Gln Lys Phe Glu
        195                 200                 205

Leu Thr Asp Lys Asn Leu Glu Ala Ala Ile Arg Lys Glu Arg Asn Cys
    210                 215                 220

Glu Leu Arg Met Ala Leu Gln Ser Val Met Lys Tyr Phe Lys Arg Lys
225                 230                 235                 240

Glu Gln Met Asn Asn Val Glu Lys Ser Asp Thr Glu Asp Asn Thr Ala
                245                 250                 255

Lys Val Asp Asp Lys Asn Asp Ala Gln Gln Gly Cys Asp Arg Lys Asp
            260                 265                 270

Lys Ser Thr Thr Gly Gly Leu Glu Glu Leu Arg Ser Val Asp Gly Glu
        275                 280                 285

Ala Glu Ala Lys Leu Thr Gly Met Leu Lys Glu Gly Glu Asn Lys Arg
    290                 295                 300

Asp Gly Lys Arg Arg Met Asp Lys Ser Pro Ser Pro Ala Ala Lys Arg
305                 310                 315                 320

Gln Lys Phe Ser Asp Val Met Lys Asp Leu Glu Ile Glu Leu Ser Glu
                325                 330                 335

Lys Leu Glu Asn Leu Ser Lys Gly Asp Leu Ala Trp Ile Asn Arg Ala
            340                 345                 350

Arg Ser Gly Arg Ile Val Lys Trp Pro Ile Leu Val Leu Lys Val Asp
        355                 360                 365

Asn Val Asn Lys Ser Cys Val Cys Thr Glu Leu Pro Leu Asp Asp Met
    370                 375                 380

Ser Ala Asn Ala Glu Trp Cys Leu Asn Ser Glu Lys Thr Arg Val Val
385                 390                 395                 400

Gln Leu Lys Asn Ile Tyr Leu Tyr Asp Thr Val Glu Ala Lys Ile Asp
                405                 410                 415

Glu Ile Glu Asp Ala Glu Leu Lys Thr Ala Ile Gln Gln Ala Asp Glu
            420                 425                 430

Ile Ala Glu Gly Ser Tyr Arg Pro Phe Asp Asp Glu Arg Asn Ser Tyr
        435                 440                 445

Asp Lys Asn Gly Asn Ser Ser Ile Arg Glu Asn Gly Cys Lys Ala Ala
    450                 455                 460

Ser Val Asn Ile Leu Ala Pro Lys Glu Ile Leu Arg Leu Cys Lys Ser
465                 470                 475                 480

Glu Met Cys Ala Arg His Leu Met Ala Ile Trp Thr Gly Gln Phe Thr
                485                 490                 495

Cys Thr Arg His Ala Gly Tyr Glu Pro Pro Phe Met Ala Pro Leu Gln
            500                 505                 510
```

```
Phe Glu Leu Asn Thr Gly Asp Leu Leu Pro Glu Thr Asp Gly Ile Ser
        515                 520                 525

Leu Val Glu His Leu Asp Ala Thr Val Ala Lys Phe Lys Asp Ala Met
    530                 535                 540

Lys Ser Ser Leu Arg Arg Leu His Tyr Val Thr Thr Val Ala Val Pro
545                 550                 555                 560

Glu Ala Ile Ile Phe Ala Ile Thr Gln Ile Arg Tyr Cys Ser Gly Ser
                565                 570                 575

Glu Ala Asn Glu Ile Phe Glu Asn Ala Leu Leu Lys Thr Val Glu Lys
            580                 585                 590

Thr Pro Ser Glu Pro Ser Asp Glu Ile Gly Ala Ala Thr Gly Phe Glu
        595                 600                 605

Gln Leu Leu Lys Ala Ala Ser Lys Val Arg Cys Ala Ala Leu Gly Met
    610                 615                 620

Asp
625


<210> SEQ ID NO 4
<211> LENGTH: 124
<212> TYPE: PRT
<213> ORGANISM: Loa loa

<400> SEQUENCE: 4

Met Leu Thr Ala Gly Met Val Glu Thr Arg Lys Tyr Glu Asn Arg Lys
1               5                   10                  15

Ile Thr Phe Gly Val Gln Thr Leu Ser Glu Asn Val Lys Asn Ile Gln
            20                  25                  30

Val Gln Ile Val Asp Ser Ile Leu Glu Arg Ile Pro Tyr Val Ile Asn
        35                  40                  45

Asn Glu Arg Glu Gln Leu Val Glu Ser Lys Trp Gly Lys Pro Tyr Val
    50                  55                  60

Leu Leu Gly Val Glu Gly Ile Ala Asp Val Val Ile Arg Asn Ser Met
65                  70                  75                  80

Lys His Pro Pro Gly Trp Met Ile Met Glu Thr Glu Val Glu Val Val
                85                  90                  95

Glu Gly Gly Lys Arg Lys Val Ala Gln Asp Ser Asp Thr Gly Asn Arg
            100                 105                 110

Asn Asp Glu Ser Tyr Lys Phe Lys Gln Leu Arg Ile
        115                 120


<210> SEQ ID NO 5
<211> LENGTH: 949
<212> TYPE: PRT
<213> ORGANISM: Loa loa

<400> SEQUENCE: 5

Met Ala Ser Ser Leu Met Asn His Thr Asn Gly Glu Leu Leu Trp Thr
1               5                   10                  15

Phe Phe Glu Asn Trp Leu Asp Glu Lys Leu Asp Ala Asn Glu Val Ile
            20                  25                  30

Val Lys Asn Thr Asp Val Lys Asn Asn Cys Lys Arg Thr His Asp Leu
        35                  40                  45

Pro Trp Lys Gly Val Thr Ile Ser Glu Ser Val Asn Lys Leu Leu Glu
    50                  55                  60

Glu Leu Ile Glu Gln Leu Ile Asp Asn Tyr Val Asn Ser Trp Tyr Lys
65                  70                  75                  80
```

```
Thr Lys Ile Ser Asp Asp Thr Thr Phe Ile Asn Glu Ile Arg Tyr Gln
                85                  90                  95

Ile Arg Tyr Ala Val Ala Val Leu Tyr Leu Arg Leu Gln Lys Ile Asp
            100                 105                 110

Leu Ser Ser Thr Ile Leu Phe Glu Ala Val Pro Leu Ala Ala Ile His
        115                 120                 125

Cys Val Arg Val Glu His Leu Arg Ala Thr Ile Asp Lys Ser Met Ser
    130                 135                 140

Ser Ser His Leu Val Glu Thr Lys Ile Leu Glu Ala Met Pro Asp Val
145                 150                 155                 160

His Phe Ala Leu Ser Ser Arg Gln Asn Glu Val Asp Tyr Leu Arg Glu
                165                 170                 175

Leu Ala Asp His Leu Ile Gly Leu Ile Met Asp Glu Arg Cys Ile Ala
            180                 185                 190

Gly His Pro Ser Asp Ser Asp Ser Pro Phe Arg Asp Ile Leu Thr Asn
        195                 200                 205

His Pro Arg Pro Trp Ala Ser His Val Cys Arg His Phe Leu Arg Glu
    210                 215                 220

Leu Phe Val Phe Ser Phe Phe Leu Pro Thr Met Asp Leu Ile Ala Asp
225                 230                 235                 240

Pro Asp Ile Ile Asn Arg Val Leu Ile Phe Leu Phe Asp Ser Asp Val
                245                 250                 255

Leu Asn Cys Pro Pro Leu Ser Gln Glu Ser Arg Gln Val Glu Ile Leu
            260                 265                 270

His Gly Leu Thr Asp Tyr Ser Leu Asn Asp Thr Pro Asp Ser Leu Leu
        275                 280                 285

Gln Leu Lys Leu Ser Asp Met Leu Arg Asp Thr Gly Gln Leu Ile Met
    290                 295                 300

Phe Arg Ala Tyr Leu Asn Asp Ile His Ala Pro Leu Asn Glu Leu Asp
305                 310                 315                 320

Phe Leu Val His Ala Gly Asp Ala His Gly Arg Met Leu Asn Val Gln
                325                 330                 335

Asn Asp Leu Val Ala Met Ser Glu Leu Gln Tyr Asp Ile Trp Glu Leu
            340                 345                 350

Phe Ile Lys Tyr Ile His Glu Gly Ala Pro Asp Arg Ile Asn Leu Pro
        355                 360                 365

Ile Glu Ile Val Cys Glu Phe Thr Glu Ala Val Glu Lys His Asp Cys
    370                 375                 380

Glu Leu Leu Asp Arg Cys Leu Glu Lys Ala Phe Gln Ile Val Tyr Lys
385                 390                 395                 400

Arg Met Gln His Glu Tyr Val Ile Pro Phe Cys Gln Ser Glu Cys Phe
                405                 410                 415

Leu Gly Asn Leu Cys Gly Pro Arg Pro Val Gly Val Asp Glu Leu Phe
            420                 425                 430

Thr Ser Arg Glu Tyr Ser Lys Ser Thr Arg Gly Leu Leu Ser Ala Val
        435                 440                 445

Glu Pro Asn Cys Ser Leu Thr Gln Phe Arg Asn Arg Phe Trp Arg Val
    450                 455                 460

Val Leu Pro Thr Ala Glu Ser Val Asp Pro Ser Phe Asp His Leu Asn
465                 470                 475                 480

Asn Val Ala Leu Ser Glu Thr Asn Ser Gly Ile Glu Pro Ala Asp Asn
                485                 490                 495

Ile Thr Glu Gly Leu Gly Ser Asp Ser Pro Asp Asp Gly Thr Thr Leu
```

```
            500                 505                 510

Pro Thr Phe Glu Phe Val Leu Asn Asn Gly Lys Glu Lys Thr Ala Glu
        515                 520                 525

Met Gln Asp Asp Gln Leu Ile Ser Asn Met Pro Asp Glu Glu Val Val
    530                 535                 540

Glu Gln Gln Met Ile Leu Ser Asn Ser Phe Glu Ile Pro Met Phe Asp
545                 550                 555                 560

Pro Glu Arg Asp Met Asn Lys Trp Asn Val Thr Phe His Met Leu Ser
                565                 570                 575

His Asp Glu Ile Leu Leu Val Val Cys His Thr Met Tyr Val Tyr Val
            580                 585                 590

Ile Ser Val Glu Arg Phe Asp Val Ser Asp Asp Ile Asp Gln Lys Ser
        595                 600                 605

Leu Ser Ala Thr Ala Ala Pro Gln Lys Trp Ser Val Ile Arg Gln Tyr
    610                 615                 620

Asn Glu Phe Tyr Ile Leu Glu Ser Lys Leu Ile Glu Phe His Gly Ser
625                 630                 635                 640

Met Ile Lys Thr Glu Ser Leu Pro Pro Arg Arg Phe Phe Asn Cys Lys
                645                 650                 655

Ser Arg Val Tyr Val Glu Ser Arg Arg Glu Ile Phe Glu Arg Phe Ile
            660                 665                 670

His Leu Leu Thr Lys Gln Arg Ala Leu Lys Gln Ser Asp Leu Leu Tyr
        675                 680                 685

Val Phe Leu Ser Thr Glu Gln Arg Leu Lys Asp Ser Thr Gln Ile Ser
    690                 695                 700

Asp Leu Tyr Pro Trp Asn Met Val Lys Lys Val Pro Gly Lys Phe Ala
705                 710                 715                 720

Arg Glu Lys Gly Gln Asn Leu Lys Pro Phe Ile Leu Ser Leu Leu Ala
                725                 730                 735

Ala Thr Leu Ile Pro His Pro Asn Asn Ser Met Glu Ser Ser Val Thr
            740                 745                 750

Ser Cys Ile His Pro Glu Ile Ala Asn Gln Thr Arg Arg Ile Leu Ala
        755                 760                 765

Ser Asp Ile Tyr Gly Asp Asn Cys Pro Ser Ala Gln Thr Asp Phe Ser
    770                 775                 780

Leu Thr Lys Ser Thr Leu Trp Thr Asn Ser Phe Tyr Asp Ala Val Leu
785                 790                 795                 800

Phe Ile Leu Asn Arg Leu Phe Gly Val Val Arg Trp Pro Ile Trp Ile
                805                 810                 815

Ile Ile Thr Ile Arg His Leu Met Gly Ser Thr Ile Asp Ala Val Ala
            820                 825                 830

Ala Val Leu Phe Arg Arg Phe Leu Ser Arg Met Phe Val Asp Ile Asn
        835                 840                 845

Cys Ile Arg Ile Leu Arg Phe Ile Gln Glu Ser Val Phe Gly Phe Asn
    850                 855                 860

Ser Ser Thr Glu Thr Asp Gln Glu Lys Met Leu Arg Met Glu Leu Ala
865                 870                 875                 880

Gln His Leu Thr Leu Glu Tyr Leu Gln Glu Gln Leu Pro Val Cys Phe
                885                 890                 895

Ile Lys Leu Ile Gly His Lys Gln Phe Ser Gln Gly Met Gln Thr Ile
            900                 905                 910

Phe Arg Ile Leu Gln Tyr Pro Arg Leu Asn Lys Gln Leu Ala Tyr Val
        915                 920                 925
```

```
Cys Leu Asp Ile Phe Ile Gln Lys Ile Phe Pro Ile Glu Asn Glu Arg
    930                 935                 940

Asn Leu Glu Ile Lys
945


<210> SEQ ID NO 6
<211> LENGTH: 104
<212> TYPE: PRT
<213> ORGANISM: Loa loa

<400> SEQUENCE: 6

Met Ala Asp Leu Ile Asp Ile Asp Asp Asp Gln Arg Arg Asn Gly Pro
1               5                   10                  15

Cys Ile Leu Tyr Asp Ala Ser Trp Ala Val Trp Ser Glu Arg Gln Ala
            20                  25                  30

Arg Ala Gln Lys Val Gln Leu Val Arg Thr Val Glu Gln Ile Asn Arg
        35                  40                  45

Gln Thr Asp Gly Leu Val Cys Tyr Val Lys Arg Lys Asp Leu Phe Gly
    50                  55                  60

Asp Leu Ser Ile Tyr Pro Trp Ala Arg Ser Ile Arg Glu Leu Val Pro
65                  70                  75                  80

Ser Ser Val Leu Ala Pro His Gln Pro Leu Glu His Phe Lys Gly Lys
                85                  90                  95

Glu Ile His Cys Ser Val Thr Trp
            100


<210> SEQ ID NO 7
<211> LENGTH: 58
<212> TYPE: PRT
<213> ORGANISM: Loa loa

<400> SEQUENCE: 7

Met Pro His Met Ser Lys Leu Ser Leu Gly Met Glu Gly Gly Ser Ser
1               5                   10                  15

Val Val Val Glu Leu Gly Ser Gly Ser Asp Leu Gln Asn Arg Pro Trp
            20                  25                  30

Thr Arg Thr Phe Ser Cys Leu Lys Val Arg Val Val Pro Leu Met Gln
        35                  40                  45

Asp Ile Ile Arg Asn Lys Pro Thr Val Ala
    50                  55


<210> SEQ ID NO 8
<211> LENGTH: 170
<212> TYPE: PRT
<213> ORGANISM: Loa loa

<400> SEQUENCE: 8

Met Lys Glu Ser Lys Leu Trp Glu Ala Ala Leu Glu Ser Ala Ile Leu
1               5                   10                  15

Ile Gly Leu Pro Ile Phe Ser Ser Pro Leu Ser Pro Leu Ser Ile Ser
            20                  25                  30

Lys Ile Pro Ala Ser Ile Ala Phe Asn Thr Lys His Leu Cys Leu Ala
        35                  40                  45

Leu Leu Val Ser Ala Phe Thr Ile Val Ala Phe Ser Ile Leu Val Arg
    50                  55                  60

Lys Met Thr Pro Lys Ile Arg Val Arg Ser Lys Val Gly Thr Pro Ile
65                  70                  75                  80
```

```
Ile Ile Arg Thr Ala Ala Thr His Lys Lys Val Arg Cys Asn Trp Pro
                85                  90                  95

Lys Ala Leu Gln Arg Pro Leu Arg Pro Val Ala Leu Lys Ile Cys Asp
            100                 105                 110

Arg Lys Ile Cys Leu Phe Leu Tyr Pro Tyr Tyr Ala Ser Phe Leu Gly
        115                 120                 125

Asn Leu Gln Pro Lys Gly Tyr Pro Gln Ser Phe Tyr Lys Ser Ile His
    130                 135                 140

Ile Ala Ile Asn Leu Asp Gly Ser Val Thr Val Met Asp Asp Gly Arg
145                 150                 155                 160

Gly Thr Asn Leu Lys Thr Leu Leu Lys Met
                165                 170


<210> SEQ ID NO 9
<211> LENGTH: 143
<212> TYPE: PRT
<213> ORGANISM: Loa loa

<400> SEQUENCE: 9

Met Lys Glu Asp Gly Lys Arg Glu Phe Val Ile His Lys Ala Ser Leu
1               5                   10                  15

Lys Ile Asn Asn Phe Ala Ile Gly Asn Ser Glu Arg Glu Pro Ile Trp
            20                  25                  30

Leu His Ser Ile Lys Ser Arg Phe His Met Gln Tyr Arg Met Pro His
        35                  40                  45

Glu Phe Ile Gly Leu Lys Ile Leu Pro Ile Ser Asn Ile Phe Arg Leu
    50                  55                  60

Leu Glu Ala Ile Val Ile Ser His Glu Val Lys His Cys Glu Met Pro
65                  70                  75                  80

Pro Gln Cys His His Arg Trp Arg Leu Lys Lys His Asn Ile Tyr Leu
                85                  90                  95

Met Ile Asn Asp Glu Asp Ser Glu Lys Ser Glu Asn Glu Met Asn Ser
            100                 105                 110

His Trp Leu Asn Ser Glu Ala Val Ser Trp Thr Asp Glu Thr Arg Asn
        115                 120                 125

Ser Phe Asp Met Met Lys Asp Thr Arg Ser Ile Val Pro Ser Ser
    130                 135                 140


<210> SEQ ID NO 10
<211> LENGTH: 96
<212> TYPE: PRT
<213> ORGANISM: Loa loa

<400> SEQUENCE: 10

Met Pro Gly Ile Gly His Leu Glu Arg Ser Gly Ser Cys Tyr Arg Thr
1               5                   10                  15

Met Lys Lys Asp Leu Arg Tyr Trp Trp Ser His Trp Val Gln Lys Ile
            20                  25                  30

Leu Lys Asn Arg Gln Asn Gln Phe Ser Arg Gly Arg Ser Glu Ser His
        35                  40                  45

Arg Pro Ser Ala Lys Pro Glu Val Phe Ser Pro Ala Cys Leu Glu Ile
    50                  55                  60

Gln Pro Pro His Ile Phe Arg Lys Asp Ser Glu Arg Ser Cys Glu Cys
65                  70                  75                  80

Pro Lys His Gly Gly Ser Ser Arg Lys Asn Asn Asp Ile Gly Asn Ser
                85                  90                  95
```

```
<210> SEQ ID NO 11
<211> LENGTH: 305
<212> TYPE: PRT
<213> ORGANISM: Loa loa

<400> SEQUENCE: 11

Met Leu Gly Ser Trp Lys Trp Ser His Gly Trp Ile Tyr Leu Gly Ser
1               5                   10                  15

Val Met Gly Ala Asp Gly Gly Thr Ile Pro Lys Arg Cys Glu Leu Val
            20                  25                  30

Lys Lys Lys Lys Lys Lys Glu Lys Leu Asp Lys Asn Val Ala Asn Thr
        35                  40                  45

Thr Arg Trp Arg Leu Cys Arg Leu Ser Gln Glu Pro Leu Lys Arg Pro
    50                  55                  60

Ile Val Ala Cys Arg Leu Gly Asn Leu Tyr Asn Lys Glu Glu Val Leu
65                  70                  75                  80

Asn Ala Ile Leu Ser Lys Lys Ile Gly Glu Tyr Glu Val Ala Met His
                85                  90                  95

Ile Arg Gly Leu Arg Asp Ile Lys Glu Leu Lys Leu Thr Asp Ser Lys
            100                 105                 110

Glu Tyr Arg Glu Ser Gly Ala Asp Lys Gly Asp Val Tyr Lys Asp His
        115                 120                 125

Asn Ile Ala Pro Phe Cys Cys Pro Val Thr Gly Ile Ser Met Asn Gly
    130                 135                 140

Asn His Pro Phe Thr Val Asn Trp Arg Cys Gly Cys Val Ile Ser Glu
145                 150                 155                 160

Lys Ala Ile Glu Glu Val Lys Pro Asp Val Cys His Gly Cys Gly Gly
                165                 170                 175

Pro Phe Ser Lys Asp Asp Leu Ile Leu Ile Asn Pro Pro Gln Asp Val
            180                 185                 190

Leu Glu Ile Tyr Lys Lys Arg Glu Glu Glu Arg Leu Lys Arg Lys Leu
        195                 200                 205

Arg Lys Thr Ala Ser Gln Glu Pro Thr Glu Lys Lys Ser Ser Met Ser
    210                 215                 220

Cys Lys Met Glu Ile Glu Ser Thr Gln Lys Lys Gly Ile Val Ser Glu
225                 230                 235                 240

Arg Lys Arg Glu Ala Ala Thr Ser Ala Asp Phe Lys Asp Leu Leu Arg
                245                 250                 255

Lys Val Glu Lys Arg Lys Ala Thr Ser Ala Lys Ile Ser Ser Ile Gln
            260                 265                 270

Asp Ser Asn Ala Ser Ala Ala Tyr Lys Ser Leu Phe Thr Thr Cys Glu
        275                 280                 285

Glu Ala Lys His Lys Pro Glu Pro His Trp Ile Thr His Asn Pro Leu
    290                 295                 300

Phe
305


<210> SEQ ID NO 12
<211> LENGTH: 100
<212> TYPE: PRT
<213> ORGANISM: Loa loa

<400> SEQUENCE: 12

Met Lys His Thr Ser Thr Leu Thr Leu Phe Phe Tyr Gly Gly Lys Arg
1               5                   10                  15
```

```
Ile Asp Lys Tyr Thr Ile Thr Ser Gln Ile Arg Arg Thr Ile Ser Glu
            20                  25                  30

Lys Ala Leu Ile Phe His Lys Leu Arg Arg Lys Gly Met Asp Phe Gly
        35                  40                  45

Ser Asn Leu Lys Lys Val Pro Arg Ile Cys Ser Ser Ile Leu Asn Trp
    50                  55                  60

Ser His Leu Gln Ala Met Arg His Ile Asn Phe Val Thr Glu Lys Ser
65                  70                  75                  80

Asn Ser Thr Met Ile Glu Leu Asn Gly Thr Val Gln Lys Asn Gln Thr
                85                  90                  95

Tyr Leu Thr Arg
            100


<210> SEQ ID NO 13
<211> LENGTH: 49
<212> TYPE: PRT
<213> ORGANISM: Loa loa

<400> SEQUENCE: 13

Met Val Arg Ile Asp Glu Asn Ile Ile Ser Gly Ala Lys Gly Ala Ser
1               5                   10                  15

Thr Val Thr Pro Arg Leu Arg Ser Gly Ala Gly Arg Glu Gly Cys Val
            20                  25                  30

Val Val Glu Tyr Val Met Ser Phe Leu Glu Gly Asp Cys Ser Cys Asn
        35                  40                  45

Pro


<210> SEQ ID NO 14
<211> LENGTH: 625
<212> TYPE: PRT
<213> ORGANISM: Loa loa

<400> SEQUENCE: 14

Met Gly Arg Lys Pro Val Arg Asn Ser Ala Pro Thr Ser Asp Leu Lys
1               5                   10                  15

Thr Gly Asp Val Val Trp Ala Pro Tyr Arg Arg Phe Pro Glu Trp Pro
            20                  25                  30

Ala Leu Val Arg Cys Val Tyr Pro Lys Lys Val Thr Tyr Thr Phe Leu
        35                  40                  45

Pro Ile Asn Glu Ser Ser Asn Leu Lys Ser Ser Ile Phe Ser Cys Pro
    50                  55                  60

Pro Gln Lys Leu Arg Leu Leu Thr Gly Asn Glu Ser Leu Pro Ala Gly
65                  70                  75                  80

Ala Lys Asn Asp Met Lys Glu Ala Tyr Lys Ala Ala Leu Glu Ile Leu
                85                  90                  95

Lys Lys Ser Gly Leu Leu Gly Ala Asp His Gln Met Ser Glu Glu Leu
            100                 105                 110

Ser Ala Phe Lys Ala Ser Glu Ile Asn Lys Gln Ser Val Leu Gly Asp
        115                 120                 125

Leu Val Lys Lys Thr Lys Lys Asp Ser Asp Ala Ala Ser Ser Gly Asp
    130                 135                 140

Thr Ala Ser Asn Ala Ser Ala Pro His Val Trp Gly Ile Gly Glu Val
145                 150                 155                 160

Val Trp Leu Ser Met Pro Asn His Ser Glu Trp Pro Val Val Ile Arg
                165                 170                 175

Glu Leu Lys Lys Lys Phe Ala Met Val Asp Ala Phe Pro Leu Lys Phe
```

```
            180                 185                 190

Asn Cys Lys Pro Glu Arg Tyr Pro Leu Ser Ala Cys Gln Lys Phe Glu
        195                 200                 205

Leu Thr Asp Lys Asn Leu Glu Ala Ala Ile Arg Lys Glu Arg Asn Cys
    210                 215                 220

Glu Leu Arg Met Ala Leu Gln Ser Val Met Lys Tyr Phe Lys Arg Lys
225                 230                 235                 240

Glu Gln Met Asn Asn Val Glu Lys Ser Asp Thr Glu Asp Asn Thr Ala
                245                 250                 255

Lys Val Asp Asp Lys Asn Asp Ala Gln Gln Gly Cys Asp Arg Lys Asp
            260                 265                 270

Lys Ser Thr Thr Gly Gly Leu Glu Glu Leu Arg Ser Val Asp Gly Glu
        275                 280                 285

Ala Glu Ala Lys Leu Thr Gly Met Leu Lys Glu Gly Glu Asn Lys Arg
    290                 295                 300

Asp Gly Lys Arg Arg Met Asp Lys Ser Pro Ser Pro Ala Ala Lys Arg
305                 310                 315                 320

Gln Lys Phe Ser Asp Val Met Lys Asp Leu Glu Ile Glu Leu Ser Glu
                325                 330                 335

Lys Leu Glu Asn Leu Ser Lys Gly Asp Leu Ala Trp Ile Asn Arg Ala
            340                 345                 350

Arg Ser Gly Arg Ile Val Lys Trp Pro Ile Leu Val Leu Lys Val Asp
        355                 360                 365

Asn Val Asn Lys Ser Cys Val Cys Thr Glu Leu Pro Leu Asp Asp Met
    370                 375                 380

Ser Ala Asn Ala Glu Trp Cys Leu Asn Ser Glu Lys Thr Arg Val Val
385                 390                 395                 400

Gln Leu Lys Asn Ile Tyr Leu Tyr Asp Thr Val Glu Ala Lys Ile Asp
                405                 410                 415

Glu Ile Glu Asp Ala Glu Leu Lys Thr Ala Ile Gln Gln Ala Asp Glu
            420                 425                 430

Ile Ala Glu Gly Ser Tyr Arg Pro Phe Asp Asp Glu Arg Asn Ser Tyr
        435                 440                 445

Asp Lys Asn Gly Asn Ser Ser Ile Arg Glu Asn Gly Cys Lys Ala Ala
    450                 455                 460

Ser Val Asn Ile Leu Ala Pro Lys Glu Ile Leu Arg Leu Cys Lys Ser
465                 470                 475                 480

Glu Met Cys Ala Arg His Leu Met Ala Ile Trp Thr Gly Gln Phe Thr
                485                 490                 495

Cys Thr Arg His Ala Gly Tyr Glu Pro Pro Phe Met Ala Pro Leu Gln
            500                 505                 510

Phe Glu Leu Asn Thr Gly Asp Leu Leu Pro Glu Thr Asp Gly Ile Ser
        515                 520                 525

Leu Val Glu His Leu Asp Ala Thr Val Ala Lys Phe Lys Asp Ala Met
    530                 535                 540

Lys Ser Ser Leu Arg Arg Leu His Tyr Val Thr Thr Val Ala Val Pro
545                 550                 555                 560

Glu Ala Ile Ile Phe Ala Ile Thr Gln Ile Arg Tyr Cys Ser Gly Ser
                565                 570                 575

Glu Ala Asn Glu Ile Phe Glu Asn Ala Leu Leu Lys Thr Val Glu Lys
            580                 585                 590

Thr Pro Ser Glu Pro Ser Asp Glu Ile Gly Ala Ala Thr Gly Phe Glu
        595                 600                 605
```

```
Gln Leu Leu Lys Ala Ala Ser Lys Val Arg Cys Ala Ala Leu Gly Met
    610                 615                 620

Asp
625


<210> SEQ ID NO 15
<211> LENGTH: 893
<212> TYPE: PRT
<213> ORGANISM: Loa loa

<400> SEQUENCE: 15

Met Ser Tyr Asn Leu Cys Lys Ile Lys Asn Leu Asp Asn Ala Glu Arg
1               5                   10                  15

Gln Ile Arg Arg Leu Glu Glu Arg Leu Arg Ala Ala Asp Leu Glu Lys
            20                  25                  30

Ala Ala Ile Glu Lys Ala Arg Lys Phe Leu Glu Glu Glu Ile Asn Lys
        35                  40                  45

Leu His Gln Gln Tyr Gln Lys Ala Thr Ala Glu Glu Glu Arg Lys Ala
    50                  55                  60

Arg Asp Lys Gln His Glu Ile Asn Leu Gly Leu Glu Glu Glu Tyr Lys
65                  70                  75                  80

Asn Arg Ile Asn Glu Leu Lys Ser Arg Ile Glu Thr Ile Gln Arg Asp
                85                  90                  95

Asn Thr Lys Leu Lys Thr Glu Leu Asn Thr Met Arg Asp Lys Tyr Arg
            100                 105                 110

Asp Thr Glu Asn Glu Tyr Asn Ile Thr Leu Arg Lys Leu Glu Glu Lys
        115                 120                 125

Asp Ala Ala Leu Arg His Leu Asp Glu Thr Lys Arg Gln Phe Thr Asn
    130                 135                 140

Glu Leu Asp Gln Gln Arg Thr Arg Tyr Asp Thr Leu Asn Ser Glu Phe
145                 150                 155                 160

Asp Arg Leu Asn Asn Glu Tyr Glu Asn Ala Asn Lys Thr Val Val Thr
                165                 170                 175

Leu Glu Gln Thr Val Arg Glu Ile Lys Gln Gln Arg Asp Glu Tyr Gly
            180                 185                 190

Lys Gln Lys Asp Glu Leu Ser Arg Gln Met Phe Asp Leu Lys His Gln
        195                 200                 205

Leu Glu Asn Glu Lys Ala Ala Arg Glu Glu Ala Glu Lys Thr Thr Ser
    210                 215                 220

Arg Leu Thr Gln Glu Ile Glu Lys Phe Lys Leu Gln Ile Thr Asp Tyr
225                 230                 235                 240

Glu Asn Gln Leu Ser Met Leu Arg Arg His Asn Asp Glu Leu Asp Thr
                245                 250                 255

Gln Ile Lys Ser Gly Gln Ala Lys Ile Thr Ala Ile Glu Asn Asp Leu
            260                 265                 270

Ile Thr Ser Gln Lys Glu Thr Val Arg Leu Asn Glu Leu Asn Ser Arg
        275                 280                 285

Leu Gln Arg Glu Lys Gln Asp Ala Ile Asn Gln Lys Leu Lys Ala Glu
    290                 295                 300

Ser Asp Ala Glu Val Trp Lys Glu Gln Ile Arg Arg Leu Glu Leu Glu
305                 310                 315                 320

Ile Glu Lys Leu Lys Ile Glu Asn Arg Thr Ile Thr Glu Gln Glu Glu
                325                 330                 335

Lys Thr Arg Asp Ala Leu Thr Lys Glu Thr Asn Arg Ala His Leu Leu
```

```
            340                 345                 350

Gln Lys Glu Leu Glu Glu Thr Lys Ala Glu Ile Glu Glu Leu Glu Lys
        355                 360                 365

Lys Ile Lys Arg Leu Glu Gln Glu Ile Glu Ser Ser Ser Arg Gly Thr
    370                 375                 380

Arg Lys Asp Glu Ser Glu Glu Thr Asp Lys Ile Ser Leu Gly Pro Ser
385                 390                 395                 400

Gly Pro Thr Val Tyr Asp Thr Glu Ile His Glu Ile Arg Ile Arg Glu
                405                 410                 415

Val Asn Asp Lys Trp Lys Leu Glu Phe Asp Lys Ile Leu Gly Glu Lys
            420                 425                 430

Asp Glu Leu Glu Arg Arg Ile Arg Asp Leu Glu Asp Gln Ile Thr Gln
        435                 440                 445

Lys Asn Arg Glu Phe Glu Arg Gln Glu Thr Glu Ile Ala Glu Leu Lys
    450                 455                 460

Arg Lys His Gln Glu Glu Ile Asp Arg Leu Arg Ser Glu Ile Ser Gln
465                 470                 475                 480

Leu His Asp Lys His Gln Asn Asp Leu Asp Asp Glu Lys Glu Gln Tyr
                485                 490                 495

Asn Lys Asn Leu Glu Ser Ile Lys Tyr Val Glu Asp Glu Leu Arg Asn
            500                 505                 510

Lys Leu Ala Glu Ala Glu Arg Lys Leu Ala Glu Ala Glu Asn Arg Glu
        515                 520                 525

Asn Gln Leu Glu Arg Glu Lys Val Glu Leu Lys Glu Lys Tyr Glu Gln
    530                 535                 540

Ala Leu Ala Gln Ile Gln Lys Leu Lys Asp Asp Leu Asp Asp Ala Arg
545                 550                 555                 560

Gln Glu Ala Glu Asn Glu Ile Gln Lys Trp Lys Thr Glu Val Tyr Ser
                565                 570                 575

Val Arg Ser Glu Leu Lys Ala Leu Glu Thr Ser Ser Asn Ala Leu Arg
            580                 585                 590

Thr Gln Leu Ala Ala Ala Asn Glu Arg Ala Glu Ser Leu Asn Lys Thr
        595                 600                 605

Val Asn Asp Gln Asn Gly Lys Ile Arg Glu Leu Asn Thr Gln Ile Arg
    610                 615                 620

Arg Leu Glu Glu Glu Ile Ser Asp Leu Lys Ser Ala Ala Val Thr Arg
625                 630                 635                 640

Glu Ser Asp Leu Glu Ser Ser Leu Ser Arg Leu Arg Ser Val Glu Asp
                645                 650                 655

Gln Tyr Ala Thr Leu Gln Ser Glu His Ala Lys Thr Arg Asn Glu Leu
            660                 665                 670

Glu Ile Leu Gln Arg Glu Tyr Asp Leu Leu Lys Ser Thr Asn Ile Asn
        675                 680                 685

Gln Glu Ser Glu Leu Glu Arg Leu Arg Asn Lys Ile Gln Gln Tyr Glu
    690                 695                 700

Val Thr Ile Lys Glu Gln Lys Asn Ala Leu Asp His Leu Lys Ala Glu
705                 710                 715                 720

Arg Glu Arg Leu Gln Asn Ile Tyr Arg Asp Lys Val Lys Gln Leu Asp
                725                 730                 735

His Leu Thr Gln Leu Val Gln Ser Phe Asp Val Lys Met Asn Lys Met
            740                 745                 750

Arg Gln Asn Leu Arg Asp Thr Ser Asp Lys Phe Val Ala Ala Glu Thr
        755                 760                 765
```

```
Glu Arg Asn Ala Leu Arg Ser Glu Val Thr Lys Leu Gln Gln Glu Leu
    770                 775                 780

Gln Phe Gly Lys Asp Gln Met Val Arg Arg Thr Asp Glu Tyr Gln Ser
785                 790                 795                 800

Ser Leu Glu Asp Leu Ala Asn Ala His Arg Ala Ala Glu Asp Gly Arg
                805                 810                 815

Leu Asn Ala Leu Gln Glu Leu Glu Ser Arg Lys Tyr Glu Leu Ala Asp
            820                 825                 830

Leu Lys Ser Arg Phe Glu Asn Thr Glu Gln Arg Leu Thr Ser Leu Gln
        835                 840                 845

His Asp Tyr Asn Lys Val Glu Asn Glu Arg Asp Ile Leu Ala Asp Ser
    850                 855                 860

Leu Lys Arg Phe Tyr Ser Val Thr Thr His Ala Val Thr Leu His Lys
865                 870                 875                 880

Val Lys Val Asn Tyr Leu Asn Glu Trp Ile Val Ile Glu
                885                 890


<210> SEQ ID NO 16
<211> LENGTH: 66
<212> TYPE: PRT
<213> ORGANISM: Loa loa

<400> SEQUENCE: 16

Met Thr Thr Arg Glu Asn Ile Cys Ser Thr Ser Phe Ser Glu Lys Glu
1               5                   10                  15

Asp His Leu Thr Gly Lys Val Ala Asn Asn Pro Val Thr Val Leu Gly
            20                  25                  30

Ser Gly Val Ala Cys Gly Lys Leu Leu Thr Ala Ser Leu Arg Arg Gln
        35                  40                  45

Thr Asp Ile Val Arg Lys Gly Val Asp Ser Lys Asp Arg Val Glu Arg
    50                  55                  60

Leu Trp
65


<210> SEQ ID NO 17
<211> LENGTH: 56
<212> TYPE: PRT
<213> ORGANISM: Loa loa

<400> SEQUENCE: 17

Ile Lys Phe Ser Lys Leu Glu Arg Arg Gln Arg Val Ser Leu Arg Leu
1               5                   10                  15

Lys Gln Ala Ala Tyr Lys Ser Val Ile Val Val Tyr Cys Glu Leu Ser
            20                  25                  30

Ser Ser Leu Gly Phe Ile Asn Gly Leu Leu Asn Gly Tyr Lys Tyr Arg
        35                  40                  45

Trp Met Thr Thr Ala Val Ile Asn
    50                  55


<210> SEQ ID NO 18
<211> LENGTH: 119
<212> TYPE: PRT
<213> ORGANISM: Loa loa

<400> SEQUENCE: 18

Met Phe Lys Gln His Ala Gln Tyr Val Gln Ser Ser Glu Ile Ile Phe
1               5                   10                  15
```

```
Asp Lys Phe Ile Asn Phe Leu Ser Ser Ser Ile Trp Asn Ile Pro Ile
            20                  25                  30

Ala Thr Phe Leu Glu Gln Tyr Ser Ile Val Phe Asp Asp Lys Gln Asn
        35                  40                  45

Asp Leu Leu Leu Tyr Gln Lys Ile His Asp Glu Phe Lys Ser Met Val
    50                  55                  60

Asp Thr Leu Met Asp Gly Phe Cys Gly Asp Leu Gln Ile Lys Ala Arg
65                  70                  75                  80

Glu Leu Val Thr Ala Leu Lys Gln His Asp Asn Ser Asn Lys Leu Ser
                85                  90                  95

Thr Lys Asn Arg Val Ala Leu Phe Phe Ser Ser Ile Asn Asn Leu Val
            100                 105                 110

Tyr Leu Ile Asn Leu Lys Leu
        115


<210> SEQ ID NO 19
<211> LENGTH: 106
<212> TYPE: PRT
<213> ORGANISM: Loa loa

<400> SEQUENCE: 19

Met Thr Leu Asp Cys Cys Arg Leu Asn Phe Gly Asp Glu Ala Leu Val
1               5                   10                  15

Leu Ala Thr Asn Ala Leu Met Ala Gln Lys Ile Asn Ala Gly Glu Arg
            20                  25                  30

Ser Ser Ile Thr Arg Gly Arg Thr Glu Asn Leu Arg Arg Arg Lys Val
        35                  40                  45

Val Ile Phe His Leu Gly Asp Val Ser Ser Leu Val Glu Leu Tyr Pro
    50                  55                  60

His Thr Ser Ile Leu Ala Asp Thr Tyr Leu Phe Asp Asn Ile Asn Ile
65                  70                  75                  80

Gly His Ile Asp Gln Tyr Ile Phe Arg Ile Ala Arg Arg Gln Arg Trp
                85                  90                  95

Trp Lys Arg Ser Arg Asn Pro Asp Ile Asp
            100                 105


<210> SEQ ID NO 20
<211> LENGTH: 93
<212> TYPE: PRT
<213> ORGANISM: Loa loa

<400> SEQUENCE: 20

Met Val Gln Pro Leu Gly Phe Gly Cys Glu Leu Asn Tyr Gly Gly Val
1               5                   10                  15

Trp Gly Gln Thr Gly His Cys Pro Phe Glu Ser Arg Gly Tyr Pro Lys
            20                  25                  30

Ala Val Gln Phe Ala Thr Met Lys Asn Val Phe Gly Gly Gln Glu Asp
        35                  40                  45

Glu Leu Pro Ala His Pro Gln Asp Pro Ile Leu Ile His Gln Lys Thr
    50                  55                  60

Phe Glu Asn Thr Thr Ile Lys Lys Cys Gln Ala Ile Glu Phe Pro Ile
65                  70                  75                  80

Gln Leu Asn Ala Thr Thr Val Asp Lys Thr Ser Arg Ile
                85                  90
```

COMPOSITIONS AND METHODS FOR DETECTING *LOA LOA*

CROSS-REFERENCE TO RELATED APPLICATIONS

This patent application is the U.S. national phase of International Patent Application No. PCT/US2016/029673, filed Apr. 28, 2016, which claims the benefit of U.S. Provisional Patent Application No. 62/153,654, filed Apr. 28, 2015, each of which is incorporated by reference in its entirety herein.

STATEMENT REGARDING FEDERALLY SPONSORED RESEARCH OR DEVELOPMENT

This invention was made with Government support under project numbers ZIAAI0000512-27 and ZIAAI000439-30 by the National Institutes of Health, National Institute of Allergy and Infectious Diseases. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 56,876 Byte ASCII (Text) file named "735794_ST25.txt," dated Oct. 13, 2017.

BACKGROUND OF THE INVENTION

*Loa loa* (African eyeworm) is a filarial nematode estimated to infect 3-13 million people in central and western Africa, and is the causative agent for loiasis. Infected individuals may exhibit a range of relatively benign symptoms. However, those who are lifelong inhabitants of endemic areas are generally asymptomatic, even with the presence of large numbers of microfilariae circulating throughout their bloodstreams. Loiasis is, nevertheless, a public health concern due to the occurrence of greater than 1,000 severe adverse reactions (including fatal encephalopathies) in *Loa*-infected individuals receiving ivermectin as a result of mass drug administration (MDA) programs aimed at the elimination of onchocerciasis and lymphatic filariasis. Consequently, disruption of further MDA has occurred in certain communities where these diseases are co-endemic.

The mechanism of *Loa*-related post-ivermectin encephalopathy is unclear, but the risk appears to be greatest with patients having blood microfilariae (mf) counts greater than about >8000 mf/ml (for non-neurological adverse events) and >25000 mf/ml (for severe, neurological adverse events). Reducing or preventing disruption of MDA therefore requires that patients with high-levels of circulating *L. loa* microfilaremia be identified and excluded from treatment. Currently available methods for detecting *Loa loa* such as, for example, microscopic evaluation of blood samples, real time quantitative polymerase chain reaction (PCR)/real time (RT)-PCR, and loop-mediated isothermal amplification (LAMP) may require sophisticated instrumentation, which may be impractical for widespread screening. Accordingly, there exists a need for improved methods for detecting the presence of *L. loa*.

BRIEF SUMMARY OF THE INVENTION

An embodiment of the invention provides a method of detecting the presence of *Loa loa* in a biological sample, the method comprising assaying the biological sample to determine the presence of one or more antigens in the biological sample, each antigen having a different amino acid sequence selected from the group consisting of SEQ ID NOs: 1-20, wherein the presence of at least one of the antigens is indicative of the presence of *Loa loa* in the biological sample.

Another embodiment of the invention provides a method comprising assaying the biological sample to determine the presence of one or more antibodies in the biological sample, each antibody specifically binding to an antigen having a different amino acid sequence selected from the group consisting of SEQ ID NOs: 1-20, wherein the presence of at least one of the antibodies is indicative of the presence of *Loa loa* in the biological sample.

Still another embodiment of the invention provides a composition comprising an immunologically-stimulatory concentration of one or more isolated or purified antigens, each antigen having a different amino acid sequence selected from the group consisting of SEQ ID NO: 1-20 and a physiologically-acceptable carrier.

Still another embodiment of the invention provides a specific binding partner that specifically binds to an antigen having an amino acid sequence selected from the group consisting of SEQ ID NO: 1-20.

An embodiment of the invention provides a method for producing an antibody that specifically binds to an antigen having an amino acid sequence selected from the group consisting of SEQ ID NO: 1-20, the method comprising administering a composition comprising an immunologically-stimulatory concentration of the inventive antigen to an animal under conditions sufficient for the animal to develop an immune response to the antigen.

Another embodiment of the invention provides a test kit comprising (a) one or more specific binding partner(s), each of which specifically binds to a different amino acid sequence selected from the group consisting of SEQ ID NO: 1-20; (b) one or more substrate(s) onto which (a) is bound or affixed; (c) one or more reagent(s) for facilitating binding of the amino acid sequence(s) to (a); and (d) one or more reagent(s) for detecting the amino acid sequence(s) specifically bound to (a).

Still another embodiment of the invention provides a test kit comprising (a) one or more antigens, each antigen having a different amino acid sequence selected from the group consisting of SEQ ID NO: 1-20; (b) one or more substrate(s) onto which (a) is bound or affixed; (c) one or more reagent(s) for facilitating binding of one or more antibodies to (a); and (d) one or more reagent(s) for detecting the antibody or antibodies specifically bound to (a).

BRIEF DESCRIPTION OF THE SEVERAL VIEWS OF THE DRAWING(S)

FIG. 1 is a graph showing the change (Δ) in optical density (O.D.) as a function of known LOAG_17808 antigen concentrations (μg/ml) in the serum of *L. loa*-infected patients as measured by an enzyme-linked immunosorbent assay (ELISA). The stars represent the amount of antigen measured in two unrelated *L. loa*-infected patients.

Figure 2A:
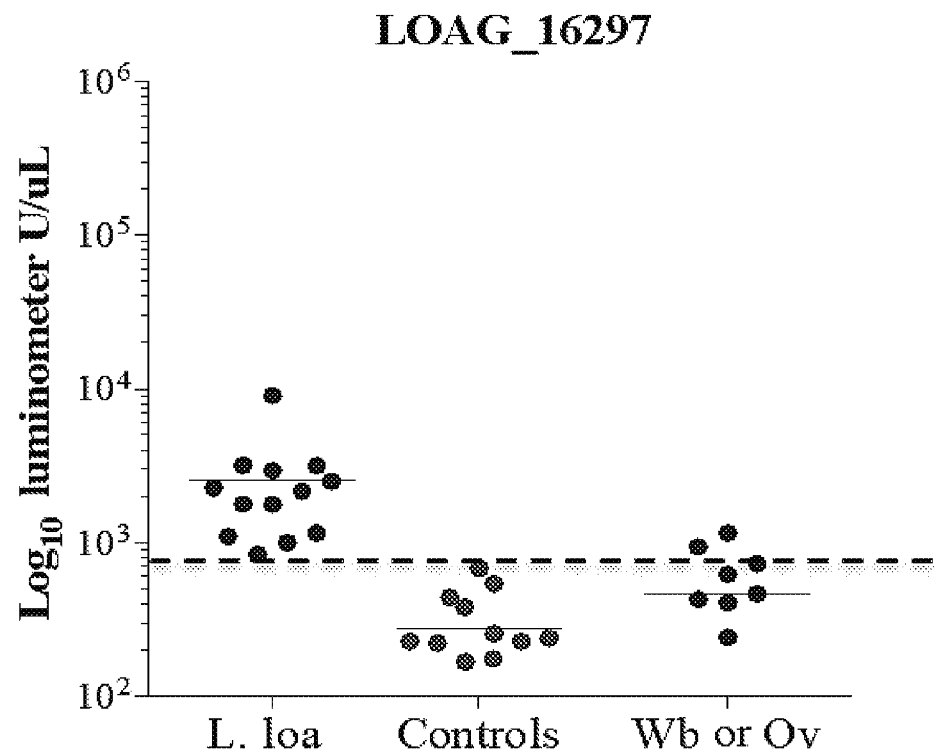
Figure 2B:
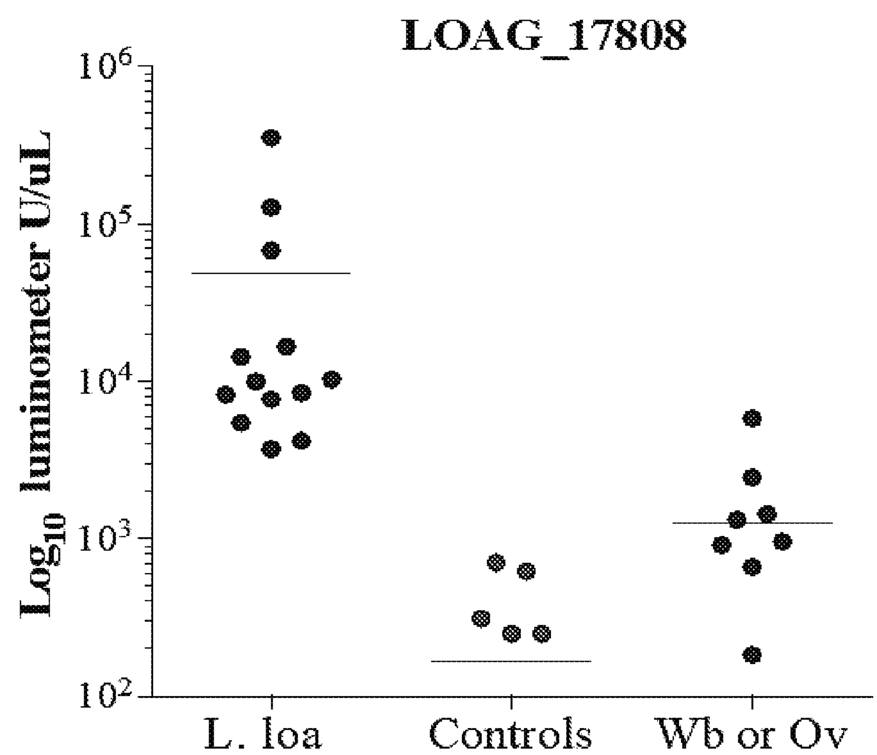

FIGS. 2A and 2B are graphs showing the specificity and sensitivity of two antigens, LOAG_16297 (SEQ ID NO: 4) (A) and LOAG_17808 (SEQ ID NO: 14) (B), when used to measure IgG antibodies against these two Ruc-antigen fusion proteins in sera from *L. loa*-infected patients, uninfected control patients, or patients infected with *Wuchereria bancrofti* (Wb) or *Onchocerca volvulus* (Ov). The dashed lines indicate the cutoff value for positivity (800 LU for LOAG_16297 (A) and 3100 LU for LOAG_17808 (B).

Figure 3B:
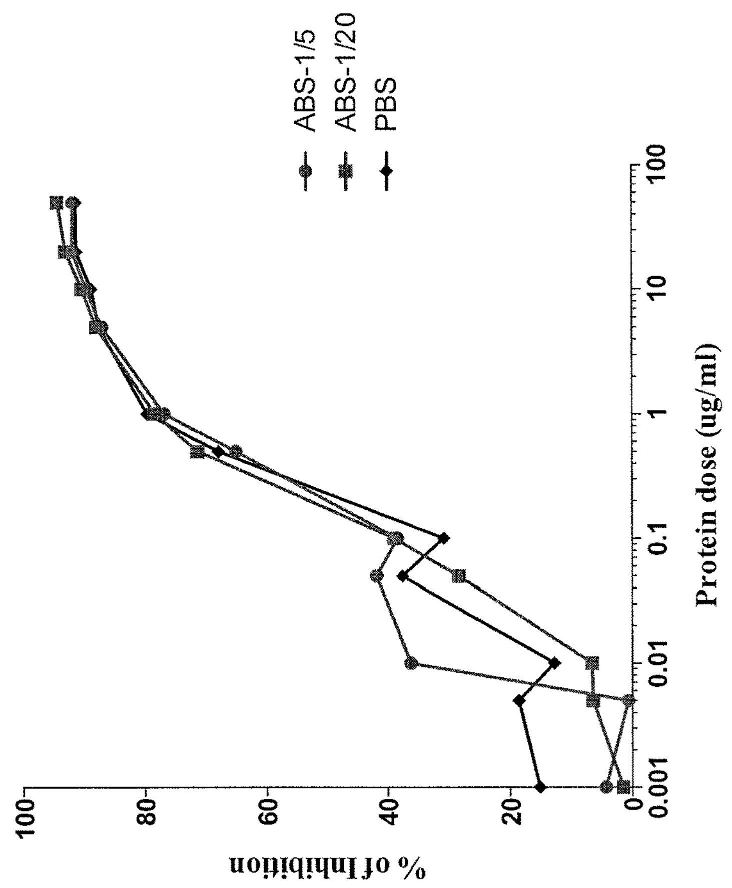
Figure 3A:
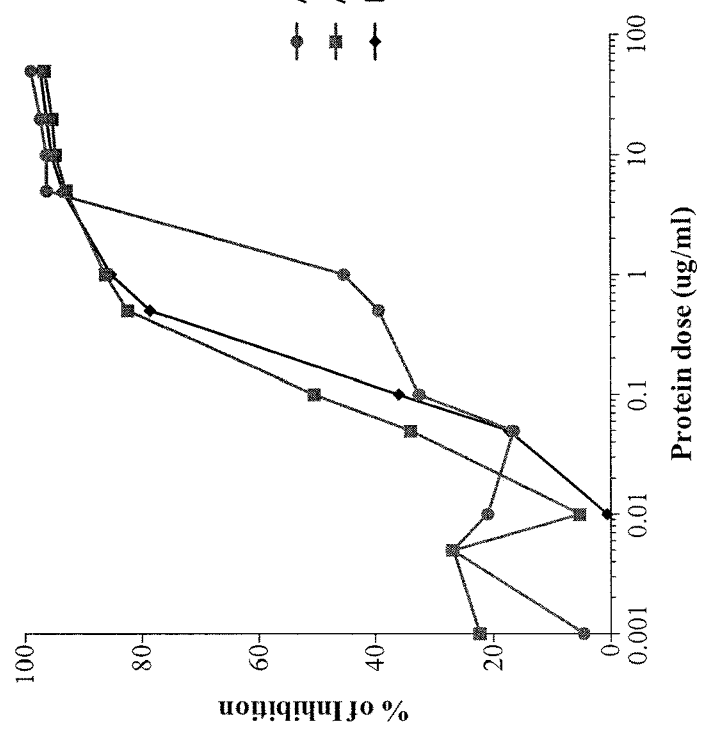

FIGS. 3A and 3B are graphs showing the percent (%) inhibition of LOAG_16297 (SEQ ID NO: 4) (A) or LOAG_17808 (SEQ ID NO: 14) (B) at various doses (μg/ml) when added to phosphate buffered saline (PBS) or human AB sera (ABS) at two different dilutions (ABS-1/5 or ABS-1/20). Data are expressed as percent inhibition in a luciferase immunoprecipitation system (LIPS)-based assay.

Figure 4:
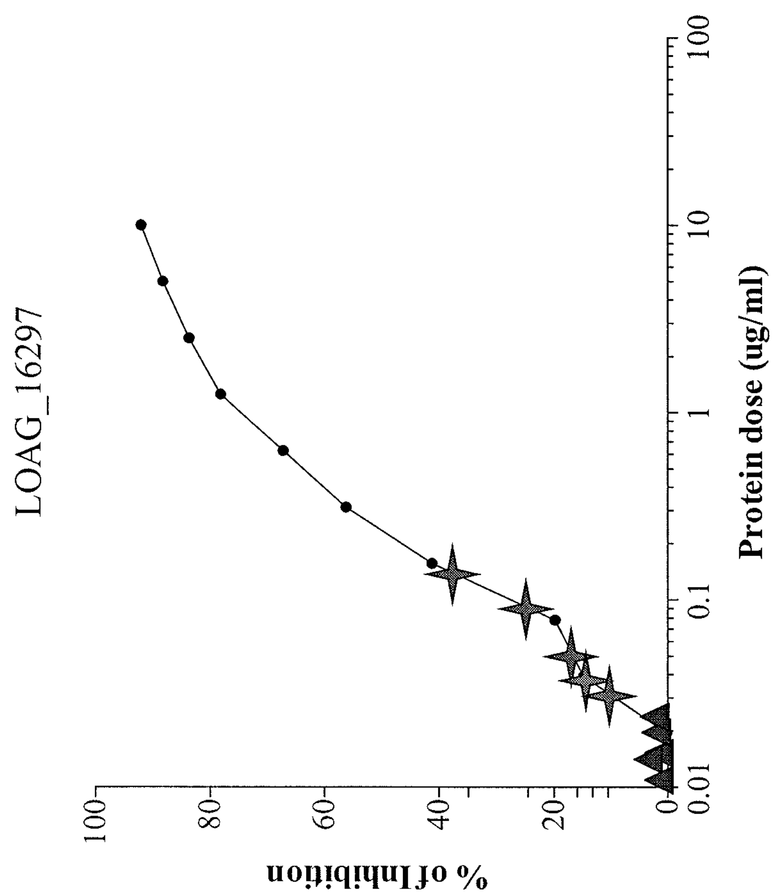

FIG. 4 is a graph showing the percent (%) inhibition by various dosages (μg/ml) of LOAG_16297 (SEQ ID NO: 4) in a LIPS-based assay. The stars represent the values (concentrations) of the specific LOAG_16297 antigens in the serum of five *L. loa*-infected patients. The triangles represent the absence of LOAG_16297 in the serum of normal individuals that are not infected with *L. loa*.

Figure 5:
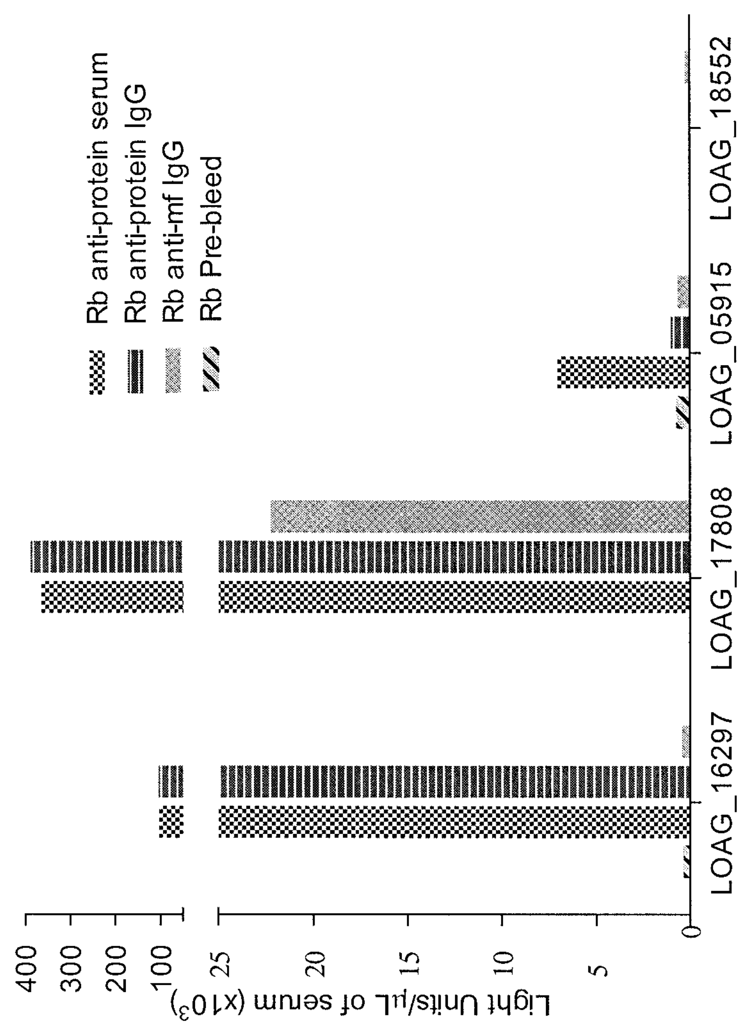

FIG. 5 is a graph showing the reactivities (measured as light units/μL of serum ($\times 10^3$)) of the four fusion proteins LOAG_16297, LOAG_17808, LOAG_05915, and LOAG_18552 to their specific antibodies in Rb anti-protein serum, Rb anti-protein IgG, Rb anti-mf IgG, or Rb pre-bleed. "Rb anti-protein serum" refers to antisera raised against the two most immunogenic peptides of each protein. "Rb anti-protein IgG" refers to the IgG purified from those antisera. "Rb anti-mf IgG" refers to purified IgG anti-*L. loa* mf somatic antigen. "Rb pre-bleed" refers to antisera collected prior to immunization. The protein names are indicated under the X-axis.

Figure 6A:
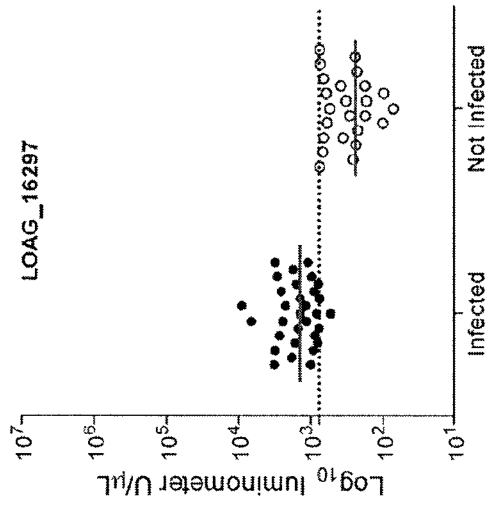
Figure 6B:
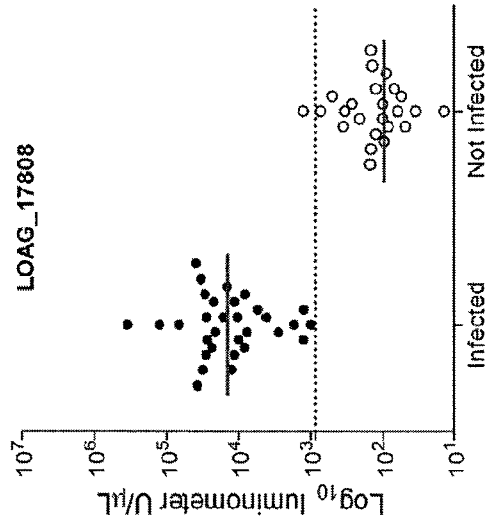
Figure 6C:
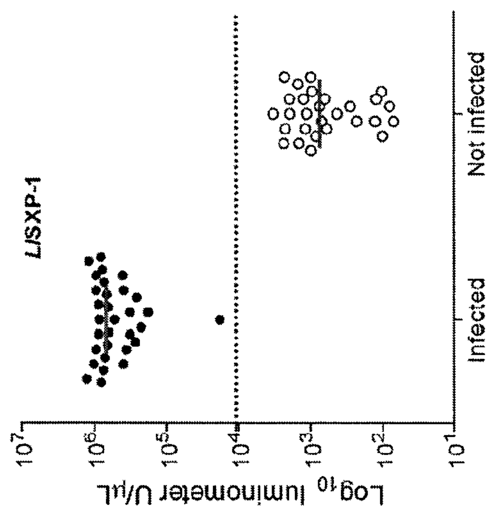

FIGS. 6A-6C are graphs showing the levels of IgG specific to LOAG_16297 (A), LOAG_17808 (B) and SXP-1 (C) as measured by light units (LU) ($Log_{10}$ luminometer U/μL) assessed by LIPS and compared between *Loa*-infected and uninfected controls. The horizontal solid line represents the median level for each group and the horizontal dotted line indicates the threshold of sensitivity/specificity of the assay determined by using a ROC analysis. Each individual is represented by a single dot with closed circles being used for the *Loa*-infected and the open circles for the uninfected individuals.

Figure 7:
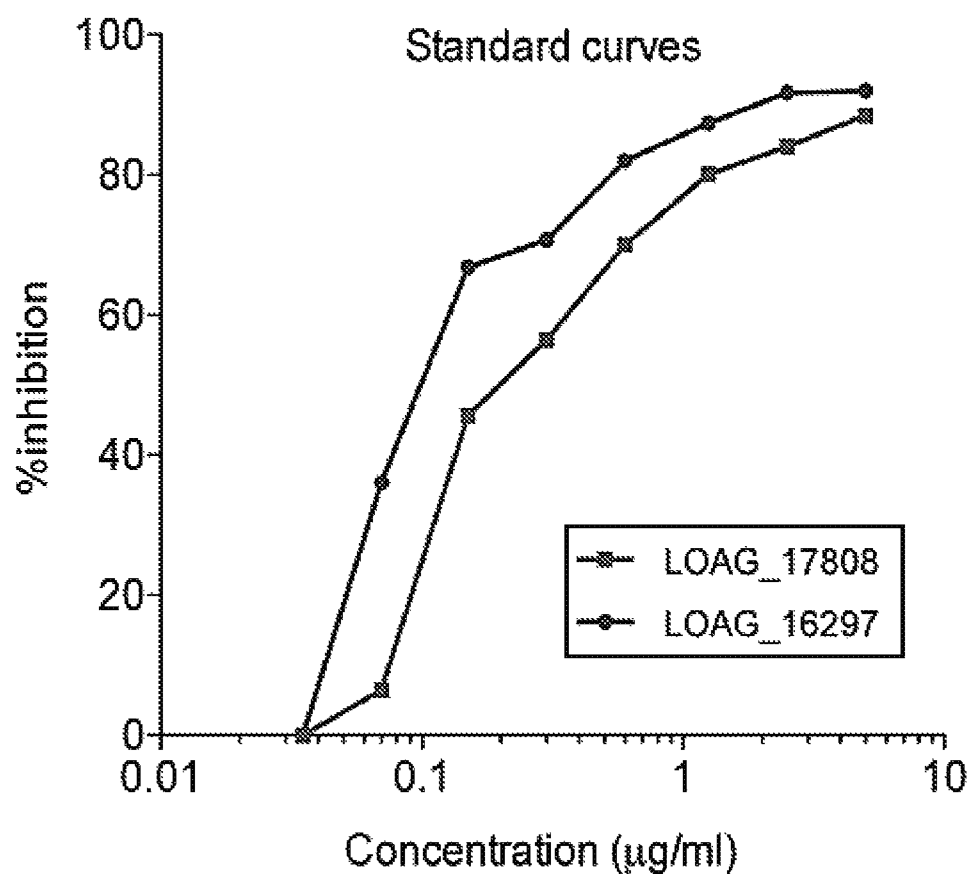

FIG. 7 is a graph showing the percent inhibition as a function of spiked recombinant protein (μg/ml) in human AB serum for LOAG_16297 (squares) and LOAG_17808 (circles).

Figure 8B:
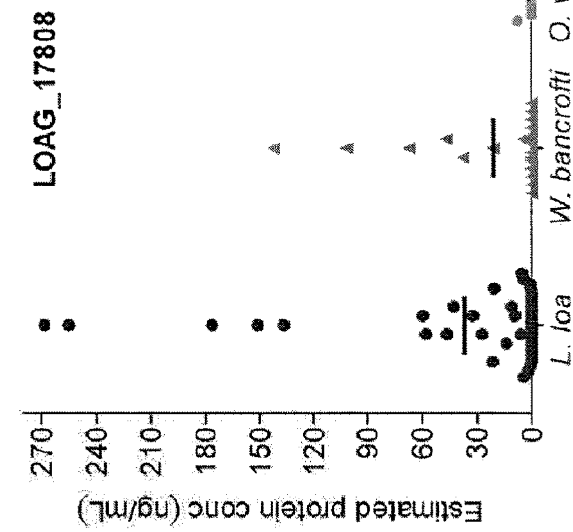
Figure 8A:
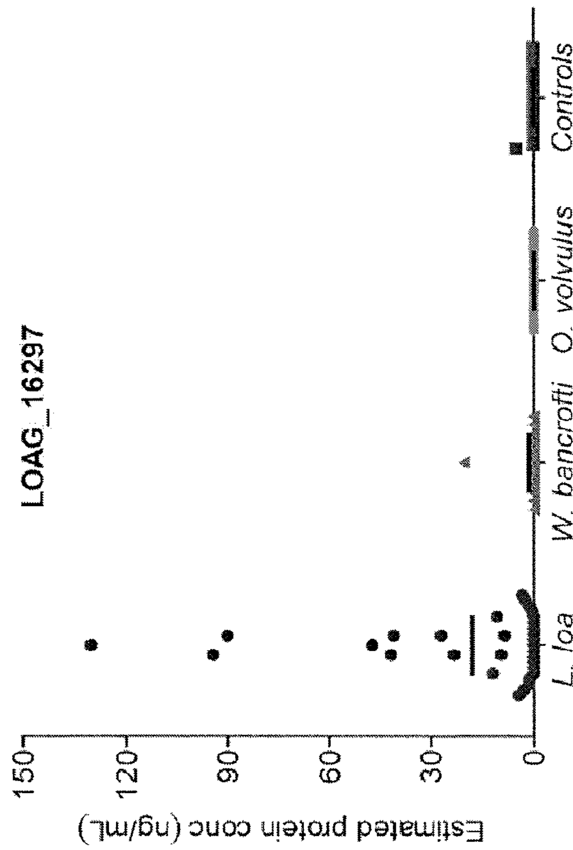

FIGS. 8A-8B are graphs showing the quantities of LOAG_16297 (A) and LOAG_17808 (B) estimated for 31 *L. loa*-, 15 *W. bancrofti*-, 15 *O. volvulus*-infected, and 25 uninfected (control) individuals extrapolated from standard curves as represented in FIG. 7. The horizontal solid black line in each group indicates the geometric mean in ng/ml of protein, and each individual value is represented by an individual dot.

Figures 9A, 9B:
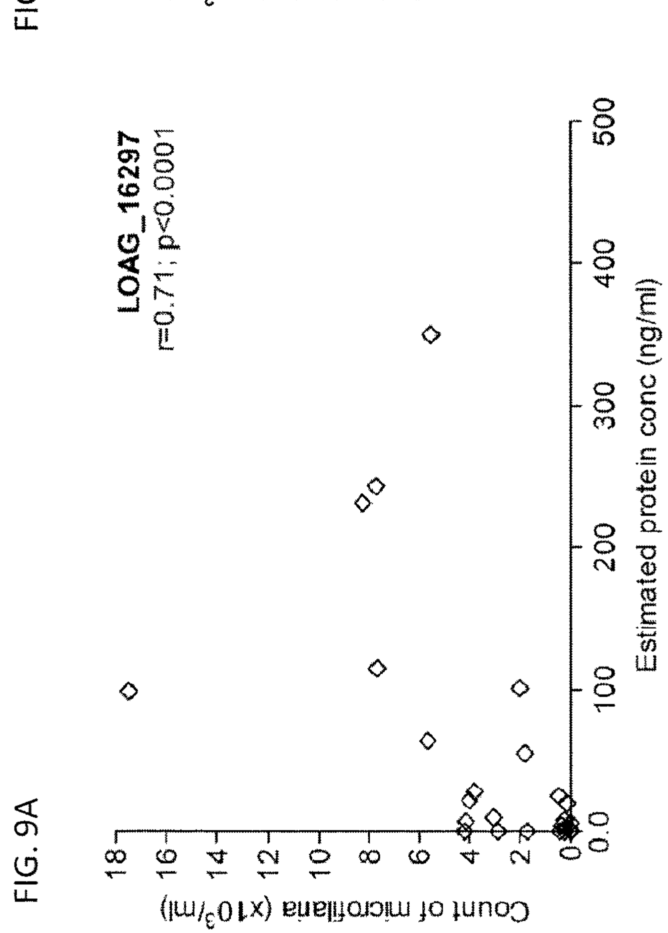

FIGS. 9A-9B are graphs showing the correlation between detected quantities of protein (estimated, ng/ml) in *L. loa* mf-infected individuals and the corresponding mf count ($\times 10^3$/ml).

DETAILED DESCRIPTION OF THE INVENTION

It has been discovered that twenty antigens having the amino acid sequences of SEQ ID NOs: 1-20, respectively, are derived from *Loa loa* microfilariae. SEQ ID NOs: 1-20 are hereinafter collectively referred to as "*Loa loa* antigens."

It is believed that these *Loa loa* antigens are unique to the microfilariae of *Loa loa* and that these antigens are not found in related filarial parasites. It has also been discovered that these *Loa loa* antigens are present in biological samples from patients that are infected with *Loa loa* and are absent from the biological samples of patients that are not infected with *Loa loa*. Accordingly, it is contemplated that these *Loa loa* antigens may be useful biomarkers for detecting and quantifying *Loa loa* in a biological sample.

The inventive methods and compositions provide many advantages. For example, the inventive methods and compositions may detect *Loa loa* more rapidly than other techniques of detecting *Loa loa* such as, for example, microscopic evaluation of blood samples, RT-PCR, and LAMP. In addition, the inventive methods and compositions may not require the sophisticated instrumentation required by other techniques such as, for example, microscopic evaluation of blood samples, RT-PCR, and LAMP. Accordingly, the inventive methods and compositions may be more practical than these techniques for wide-spread screening, particularly in resource-limited geographical regions.

An embodiment of the invention provides a method of detecting the presence of *Loa loa* in a biological sample. The method may comprise assaying the biological sample to determine the presence of one or more antigens in the biological sample, each antigen having a different amino acid sequence selected from the group consisting of SEQ ID NOs: 1-20. In an embodiment of the invention, each antigen has a different amino acid sequence selected from the group consisting of SEQ ID NOs: 1-14. The assaying may involve using a specific binding partner that preferentially binds to one of the inventive *Loa loa* antigens, or two or more (for example, 1, 2, 3, 4, 5, 6, 7, 8, 9, 10, 11, 12, 13, 14, 15, 16, 17, 18, 19, or 20) binding partners that each preferentially binds to a different inventive *Loa loa* antigen. For example, the assaying can involve the use of a first specific binding partner that can preferentially, e.g., specifically, bind to an antigen having the amino acid sequence of SEQ ID NO: 4, a second specific binding partner that can preferentially/specifically bind to an antigen having the amino acid sequence of SEQ ID NO: 14, or both of said first and said second specific binding partners, and so on. In this regard, in an embodiment of the invention, the method comprises assaying the biological sample to determine the presence of two or more antigens, each antigen having a different amino acid sequence selected from the group consisting of SEQ ID NOs: 1-20 in the biological sample, wherein the presence of at least two of the antigens is indicative of the presence of *Loa loa* in the biological sample. In an embodiment of the invention, each antigen has a different amino acid sequence selected from the group consisting of SEQ ID NO: 1-14. In an embodiment of the invention, the two antigens have the amino acid sequences of SEQ ID NOs: 4 and 14, respectively.

In an embodiment of the invention, the method comprises (a) contacting the biological sample with one or more specific binding partner(s), each of which specifically binds to a different amino acid sequence selected from the group consisting of SEQ ID NOs: 1-20, thereby forming one or more complexes; and (b) detecting the one or more complexes, wherein detection of the one or more complexes is indicative of *Loa loa* in the biological sample. In an embodiment of the invention, each specific binding partner binds to a different amino acid sequence selected from the group consisting of SEQ ID NO: 1-14.

In still another embodiment of the invention, method comprises (a) contacting the biological sample with two or more specific binding partner(s), each of which specifically binds to a different amino acid sequence selected from the group consisting of SEQ ID NOs: 1-20, thereby forming two or more complexes; and (b) detecting the two or more complexes, wherein detection of the two or more complexes is indicative of *Loa loa* in the biological sample. In an embodiment of the invention, each specific binding partner specifically binds to a different amino acid sequence selected from the group consisting of SEQ ID NOs: 1-14. In an embodiment of the invention, the two specific binding partners specifically bind to antigens having the amino acid sequences of SEQ ID NOs: 4 and 14, respectively.

Contacting may comprise physically contacting the biological sample with the specific binding partner(s) under conditions that facilitate the formation of one or more complexes including the binding partner(s) bound, respectively, to any of the *Loa loa* antigens described herein. The method may further comprise washing any unbound specific binding partner and any unbound antigen from the one or more complexes.

Detecting the one or more complexes can be carried out through any number of ways known in the art. For instance, the one or more binding partners can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Using such specific binding partners that can specifically/preferentially bind to an antigen having an amino acid sequence selected from the group consisting of SEQ ID NOs: 1-20 (or two or more specific binding partners, each specifically binding to a different *Loa loa* antigen), the assaying can use immunochemical methods to detect the presence of one (or two or more) antigens of SEQ ID NOs: 1-20 in the biological sample. Such types of assays are known to persons of ordinary skill in the art and include methods such as immunoprecipitation, immunonephelometry, radioimmunoassay (RIA), enzyme immunoassay (EIA), fluorescent immunoassay (FIA), luciferase immunoprecipitation system (LIPS), and lateral flow immunochromatographic assay (also referred to as "lateral flow test") and the like.

Preferably, the assay employed in the inventive method using one or more specific binding partner(s) is an enzyme-linked immunosorbent assay (ELISA) or enzyme immunoassay (EIA) (e.g., sandwich ELISA). In this regard, an embodiment of the invention provides a method comprising (a) contacting the biological sample with a first specific binding partner that specifically binds to one of the antigens, thereby forming a first complex; (b) contacting the first complex with a second specific binding partner that specifically binds to the first complex, thereby forming a second complex; and (c) detecting the second complex, wherein detection of the second complex is indicative of the presence of *Loa loa* in the biological sample. In an embodiment of the invention, the first specific binding partner is a first antibody, or an antigen binding fragment thereof, and the second specific binding partner is a second antibody, or an antigen binding fragment thereof, as described herein with respect to other aspects of the invention.

The contacting of the biological sample with a first specific binding partner and forming a first complex may be carried out as described herein with respect to other aspects of the invention. Contacting the first complex with a second specific binding partner may comprise physically contacting the first complex with the second specific binding partner under conditions that facilitate the formation of a second complex including the second binding partner bound to the first complex. The method may further comprise washing any unbound binding partner and any unbound antigen from the second complex. Detecting the second complex may be carried out as described herein with respect to other aspects of the invention.

The presence of one (or more) antigens of SEQ ID NOs: 1-20 in the biological sample indicates that *Loa loa* is present in the biological sample and in the mammal from which the biological sample was obtained. In an embodiment of the invention, the presence of one (or more) antigens of SEQ ID NOs: 1-14 in the biological sample indicates that *Loa loa* is present in the biological sample and in the mammal from which the biological sample was obtained.

The biological sample may be any suitable biological sample from any mammal. In an embodiment of the invention, the biological sample is whole blood, serum, plasma, urine, or saliva.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. Preferably, the biological sample is a human biological sample.

A "specific binding partner" is a molecule that can bind with measurably higher affinity to one of the *Loa loa* antigens than to other molecules. In an embodiment of the invention, the specific binding partner is an antibody (also referred to herein as an "immunoglobulin") or an antigen-binding fragment of the antibody. The antibody for use in the inventive method can be of any type. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

In an embodiment, the specific binding partner is an antigen binding fragment of any of the antibodies described herein. The antigen binding fragment can be any fragment of the antibody that has at least one antigen binding site. In an embodiment, the antigen binding fragment is a Fab fragment (Fab), F(ab')2 fragment, diabody, triabody, tetrabody, single-chain variable region fragment (scFv), or disulfide-stabilized variable region fragment (dsFv). A single-chain variable region fragment (scFv), which is a truncated Fab fragment including the variable (V) domain of an antibody heavy chain linked to a V domain of a light antibody chain via a synthetic antigen, can be generated using routine recombinant DNA technology techniques (see, e.g., Murphy et al. (eds.), *Janeway's Immunobiology,* 8$^{th}$ Ed., Garland Science, New York, N.Y. (2011)). Similarly, disulfide-stabilized variable region fragments (dsFv) can be prepared by recombinant DNA technology. The antibody fragments of the invention, however, are not limited to these exemplary types of antibody fragments.

It is contemplated that a mammal infected with *Loa loa* may produce one or more antibodies, each of which specifically binds to an antigen having a different amino acid sequence selected from the group consisting of SEQ ID NOs: 1-20. It is contemplated that a mammal infected with

*Loa loa* may produce one or more antibodies, each of which specifically binds to an antigen having a different amino acid sequence selected from the group consisting of SEQ ID NOs: 1-14. Accordingly, it is believed that detecting antibodies in the biological sample that specifically bind to one or more of the *Loa loa* antigens described herein may indicate the presence of *Loa loa* in the biological sample.

In this regard, another embodiment of the invention provides a method of detecting the presence of *Loa loa* in a biological sample, the method comprising assaying the biological sample to determine the presence of one or more antibodies in the biological sample, each antibody specifically binding to an antigen having a different amino acid sequence selected from the group consisting of SEQ ID NOs: 1-20, wherein the presence of at least one of the antibodies is indicative of the presence of *Loa loa* in the biological sample. In an embodiment of the invention, each antibody specifically binds to an antigen having a different amino acid sequence selected from the group consisting of SEQ ID NOs: 1-14.

The assaying for the presence of antibodies may be carried out as described herein with respect to other aspects of the invention. In an embodiment of the invention, the method comprises (a) contacting the biological sample with one or more antigens, each having a different amino acid sequence selected from the group consisting of SEQ ID NOs: 1-20, thereby forming one or more complexes with one or more antibodies, each antibody specifically binding to a different antigen, and (b) detecting the one or more complexes, wherein detection of the one or more complexes is indicative of *Loa loa* in the biological sample. In an embodiment of the invention, each antigen has a different amino acid sequence selected from the group consisting of SEQ ID NOs: 1-14. The contacting may be carried out as described herein with respect to other aspects of the invention. The method may further comprise washing unbound antibody or unbound antigen, as described herein with respect to other aspects of the invention.

Detecting the complex can be carried out through any number of ways known in the art. For instance, the inventive *Loa loa* antigens can be labeled with a detectable label as described herein with respect to other aspects of the invention.

Two or more antibodies, each antibody binding to a different amino acid sequence selected from the group consisting of SEQ ID NOs: 1-20, may be detected in the biological sample. In this regard, an embodiment of the invention provides a method comprising assaying the biological sample to determine the presence of two or more antibodies in the biological sample, each antibody specifically binding to an antigen having a different amino acid sequence selected from the group consisting of SEQ ID NOs: 1-20, wherein the presence of at least two of the antibodies is indicative of the presence of *Loa loa* in the biological sample. In an embodiment of the invention, each antibody binds to a different amino acid sequence selected from the group consisting of SEQ ID NOs 1-14. In an embodiment of the invention, the two antibodies specifically bind to antigens having the amino acid sequences of SEQ ID NOs: 4 and 14, respectively.

In an embodiment of the invention, the antigen is a first antigen, and the method further comprises (a) contacting the biological sample with a second antigen having an amino acid sequence selected from the group consisting of SEQ ID NOs: 1-20, thereby forming a second complex with a second antibody that specifically binds to the second antigen, and (b) detecting the second complex, wherein detection of the second complex is indicative of *Loa loa* in the biological sample, and wherein the first and second antigens have different amino acid sequences. In an embodiment of the invention, the method comprises contacting the biological sample with a second antigen having an amino acid sequence selected from the group consisting of SEQ ID NOs: 1-14. In an embodiment of the invention, the two antigens have the amino acid sequences of SEQ ID NOs: 4 and 14, respectively. The contacting and detecting may be carried out as described herein with respect to other aspects of the invention.

In an embodiment of the invention, the methods of detecting *Loa loa* described herein may further comprise quantifying the number of *Loa loa* organisms present in the biological sample. For example, the method may comprise quantifying the number of *Loa loa* microfilariae in the biological sample. Quantification of the *Loa loa* may be carried out using routine techniques. In an embodiment of the invention, quantifying the *Loa loa* comprises determining the amount of detectable label present. For example, the method may comprise determining the amount of fluorescence or luminescence provided by the detectable label. In an embodiment of the invention, quantification may comprise carrying out any of the methods of detecting *Loa loa* described herein in (1) a test biological sample in which the quantity of *Loa loa* is unknown and (2) a positive control biological sample having a known quantity of *Loa loa*. The quantity of *Loa loa* in the test biological sample may be estimated by comparing the quantity of label detected in the test biological sample to that detected in the positive control biological sample.

In another aspect, the invention provides reagents for generating antibodies that can specifically (e.g., preferentially) bind to any one of SEQ ID NOs: 1-20. In this respect, the invention provides a composition comprising an immunologically-stimulatory concentration of at least one isolated or purified antigen, each antigen having a different amino acid sequence selected from the group consisting of SEQ ID NO: 1-20 and a physiologically-acceptable carrier. An embodiment of the invention provides a composition comprising an immunologically-stimulatory concentration of at least one isolated or purified antigen, each antigen having a different amino acid sequence selected from the group consisting of SEQ ID NO: 1-14 and a physiologically-acceptable carrier. The composition can be administered to an animal (typically a mouse, goat, rabbit, or other animal commonly employed for generating antibodies). The immunologically-stimulatory concentration of the composition is sufficiently concentrated to challenge the immune system of the animal with one or more (e.g., 1, 2, 3, 4, 5, 6, 7, 8, 9, 10, 11, 12, 13, 14, 15, 16, 17, 18, 19, or 20) of SEQ ID NOs: 1-20 present in the composition. The physiological carrier can be a buffered saline or other media typically employed to administer antigenic substances for the production of antibodies. The composition also can comprise one or more adjuvants to assist the animal in mounting an immune reaction to one or more of SEQ ID NOs: 1-20 present in the composition to increase the likelihood that antibodies capable of specifically binding to such antigens will be generated. In an embodiment of the invention, the composition also can comprise one or more adjuvants to assist the animal in mounting an immune reaction to one or more of SEQ ID NOs: 1-14.

Many assays for determining an immunologically-stimulatory concentration are known in the art. For purposes of the invention, an assay, which comprises comparing the extent to which antibodies are secreted by B cells in the mammal upon administration of a given concentration of the one or more of SEQ ID NOs: 1-20, respectively, to a mammal among a set of mammals in which each is given a different concentration of the one or more of SEQ ID NOs: 1-20, respectively, could be used to determine a starting concentration to be administered to a mammal. The extent to which antibodies are secreted by B cells upon administration of a certain concentration can be assayed by methods known in the art.

Thus, using such immunological compositions, the invention provides a method of producing one or more antibodies, each antibody specifically (e.g., preferentially) binding to an antigen having a different amino acid sequence selected from the group consisting of SEQ ID NOs: 1-20 by administering (e.g., by intravenous injection or other suitable route) the composition comprising the immunologically-stimulatory concentration of the one or more of SEQ ID NOs: 1-20, respectively, and a physiologically-acceptable carrier to an animal under conditions sufficient for the animal to develop an immune response to the one or more of SEQ ID NOs: 1-20, respectively. An embodiment of the invention provides a method of producing one or more antibodies, each antibody specifically (e.g., preferentially) binding to an antigen having a different amino acid sequence selected from the group consisting of SEQ ID NOs: 1-14 by administering (e.g., by intravenous injection or other suitable route) the composition comprising the immunologically-stimulatory concentration of the one or more of SEQ ID NOs: 1-14, respectively, and a physiologically-acceptable carrier to an animal under conditions sufficient for the animal to develop an immune response to the one or more of SEQ ID NOs: 1-14, respectively. In this context, the animal's immune response includes the generation of one or more antibodies, each antibody specifically (e.g., preferentially) binding to an antigen having a different amino acid sequence selected from the group consisting of SEQ ID NOs: 1-20.

Standard immunological techniques can be employed in producing antibodies that can specifically (e.g., preferentially) bind to any one of SEQ ID NOs: 1-20, respectively, in accordance with the present invention. For example, once the animal is inoculated and has developed the immune response (producing one or more antibodies, each antibody specifically binding to an antigen having a different amino acid sequence selected from the group consisting of SEQ ID NOs: 1-20), serum can be harvested from the animal which comprises the antibody or antibodies of interest. The serum can be further processed, if desired, to concentrate or stabilize the antibody or antibodies. The resulting composition is typically a polyclonal antibody composition.

Alternatively, once the animal is inoculated and has developed the immune response (producing one or more antibodies, each antibody specifically binding to an antigen having a different amino acid sequence selected from the group consisting of SEQ ID NOs: 1-20 or producing one or more antibodies, each antibody specifically binding to an antigen having a different amino acid sequence selected from the group consisting of SEQ ID NOs: 1-14), one or more splenocytes can be harvested from the animal, which can then be fused with one or more immortal cell(s) (e.g., myeloma cells) to form one or more hybridomas. The hybridoma is then cultured (and typically proliferated into a population), such that it then secretes the antibodies that can specifically (e.g., preferentially) bind to one or more of SEQ ID NOs: 1-20, respectively, into the culture media in which the hybridoma is grown. The culture medium can then be harvested and further processed, if desired, to concentrate or stabilize the antibody or antibodies. Also, the hybridomas can be cultured initially, or subcultured, at a sufficiently dilute density to establish clonal populations, which can facilitate the production of monoclonal antibodies. Standard hybridoma methods are described in, e.g., Murphy, supra, and *Antibodies: A Laboratory Manual,* 2nd Ed., CSH Press (2013).

The affinity of binding of the resulting antibodies can be assessed, for example, by exposing a substrate coated or impregnated with one of SEQ ID NOs: 1-20 to the putative specific binding partner (e.g., an antibody) and exposing a negative control (e.g., a blank substrate and/or one coated with or impregnated with another molecule (e.g., albumin)) to the putative specific binding partner under like conditions. It will be understood that the substrate(s) can be the same, such as a Western blot having spots or bands of several molecules. After exposure to the putative specific binding partner, the substrate(s) can be washed to remove non-specific binding and then the presence of the specific binding partner bound to one of SEQ ID NOs: 1-20 can be verified, e.g., by using a labeled secondary antibody or other suitable technique.

The antibodies produced in accordance with the present invention can be derivitized to produce other specific binding partners for specifically binding one of SEQ ID NOs: 1-20 (e.g., an antigen binding portion of the antibody as described herein with respect to other aspects of the invention). Also, if desired, the antibodies and other specific binding partners that can specifically bind one of SEQ ID NOs: 1-20 can be bound to or conjugated with a detectable label as described herein with respect to other aspects of the invention.

Phage display furthermore can be used to generate an antibody. In this regard, phage libraries encoding antigen-binding variable (V) domains of antibodies can be generated using standard molecular biology and recombinant DNA techniques. See, for instance, Green et al. (eds.), *Molecular Cloning. A Laboratory Manual,* 4$^{th}$ Edition, Cold Spring Harbor Laboratory Press, New York (2012) and Ausubel et al., *Current Protocols in Molecular Biology*, Greene Publishing Associates and John Wiley & Sons, NY (2007). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Murphy et al., supra).

Another embodiment of the invention provides a specific binding partner that specifically binds to an antigen having an amino acid sequence selected from the group consisting of SEQ ID NO: 1-20. Another embodiment of the invention provides a specific binding partner that specifically binds to an antigen having an amino acid sequence selected from the group consisting of SEQ ID NO: 1-14. Preferably, the specific binding partner is an antibody, or antigen-binding fragment thereof.

The inventive antibody (or antibodies) and other specific binding partner(s) for specifically binding one of SEQ ID NOs: 1-20 can be employed as reagents in standard immunochemical assays for the detection of SEQ ID NOs: 1-20, respectively, such as from a biological sample as described herein. Thus, another embodiment of the present invention provides a composition comprising one or more antibodies or other specific binding partner(s) that can specifically (e.g., preferentially) bind to SEQ ID NOs: 1-20, respectively, in isolated form or including a carrier. Another embodiment of the present invention provides a composition comprising one or more antibodies or other specific binding partner(s) that can specifically (e.g., preferentially) bind to SEQ ID NOs: 1-14, respectively, in isolated form or including a carrier. The carrier can be aqueous and include buffers, preservatives, chelating agents, if desired, to enhance stability and to facilitate their use in immunochemical assays.

The inventive antigens, antibodies, and specific binding partners described herein can be of synthetic or natural origin, and can be isolated or purified to any degree. The terms "isolated" and "purified," as used herein, means having been removed from its natural environment. The term "purified" or "isolated" means having been increased in purity and does not require absolute purity or isolation; rather, it is intended as a relative term. For example, the purity can be at least about 50%, can be greater than about 60%, about 70% or about 80%, or can be about 100%.

An embodiment of the invention also provides a test kit comprising the inventive antibody (or antibodies) and other specific binding partner(s) that can specifically (e.g., preferentially) bind to SEQ ID NOs: 1-20, respectively. An embodiment of the invention also provides a test kit comprising the inventive antibody (or antibodies) and other specific binding partner(s) that can specifically (e.g., preferentially) bind to SEQ ID NOs: 1-14, respectively. The test kit can include, for example, one or more substrate(s) onto which the specific binding partner(s) is/are bound or affixed, one or more reagent(s) for facilitating binding of one or more of SEQ ID NOs: 1-20 (or one or more of SEQ ID NOs: 1-14) within a sample to the specific binding partner(s), one or more reagent(s) for detecting the amino acid sequence(s) specifically bound to the specific binding partner(s) (e.g., one or more secondary antibody(ies) that can specifically bind to the antigen or specific binding partner(s), which can be conjugated to an enzymatic substrate moiety, fluorescent moiety, or radioactive moiety, as well as suitable enzymes and apparatus for detecting the fluorescence or radioactivity, respectively), and other materials and reagents commonly employed in immunochemical diagnostic test kits and apparatus.

Another embodiment of the invention also provides a test kit comprising one or more antigens, each antigen having a different amino acid sequence selected from the group consisting of SEQ ID NOs: 1-20 that can specifically bind to one or more antibodies in a biological sample. Another embodiment of the invention also provides a test kit comprising one or more antigens, each antigen having a different amino acid sequence selected from the group consisting of SEQ ID NOs: 1-14 that can specifically bind to one or more antibodies in a biological sample. The test kit can include, for example, one or more substrate(s) onto which the antigen(s) is/are bound or affixed, one or more reagent(s) for facilitating binding of one or antibodies within a sample to one or more of SEQ ID NOs: 1-20, respectively, one or more reagent(s) for detecting the antibody specifically bound to the antigen (e.g., one or more secondary antibody (antibodies)) that can specifically bind to the antigen or antibody, as described herein with respect to other aspects of the invention, and other materials and reagents commonly employed in immunochemical diagnostic test kits and apparatus.

The following examples further illustrate the invention but, of course, should not be construed as in any way limiting its scope.

EXAMPLES

The following materials and methods were employed for the experiments described in Examples 1-8.

Study Population and Samples

Samples were collected from subjects as part of registered protocols approved by the Institutional Review Boards of the National Institute of Allergy and Infectious Diseases for the filarial-infected patients (NCT00001345) and for the healthy donors (NCT00090662). Written informed consent was obtained from all subjects.

Urine from one microfilaremic (17,000 mf/ml) *L. loa*-infected patient assessed at the NIH Clinical Center and one normal North American donor (who had never traveled outside the USA) was used for the profiling of specific *L. loa* mf proteins by using RPLC-MS/MS (reverse phase liquid chromatography tandem mass spectrometry).

Plasma samples used to validate the utility of potential biomarkers were from *L. loa*-infected individuals (n=31 [26 being microfilaremic and 5 amicrofilaremic]). Samples used as controls included subjects with *W. bancrofti* (mf+; n=15) from India and the Cook Islands (both non-endemic for *L. loa*), those with *O. volvulus* (mf+; n=15) infection from Ecuador (non-endemic for *L. loa*) and those from North America (n=31) that had no history of exposure to filarial or other helminths and who had never traveled outside of North America. The parasitological diagnosis of all infections was made based on the demonstration of mf in the blood (for *W. bancrofti* and *L. loa*) or in the skin (for *O. volvulus*) using standard techniques (Moody et al., *Clin. Lab. Haematol.*, 22: 189-201 (2000); Dickerson et al., *J. Parasitol.*, 76: 829-833 (1990)) or by finding adult parasites in the tissues (e.g. the eye for *L. loa*).

Sample Preparation Prior to Mass Spectrometric Analysis

Urine samples were processed according to a workflow adapted from Nagaraj et al., *J. Proteome Res.*, 10: 637-645 (2011). Briefly, urine samples were centrifuged for 15 minutes (mins) at 4° C. and the supernatant was concentrated using a spin-filter with a molecular weight cut off 3 KDa. Proteins were precipitated by acetone precipitation and subsequently treated in 10 mM Tris-HCl at 95° C. for 5 mins. The samples were then reduced, alkylated and double digested with Lys-C in combination with trypsin overnight at 37° C. Tryptic peptides were further desalted, lyophilized and reconstituted in 25% acetonitrile with 0.1% formic acid and further fractionated using strong cation exchange (SCX) chromatography. The SCX fractions of the urine samples were pooled into 32 fractions, lyophilized and reconstituted in 0.1% TFA (trifluoroacetic acid) to be analyzed by LCMS (liquid chromatography-mass spectrometry).

Nanobore Reversed-Phase Liquid Chromatography Tandem MS

Nanobore RPLC-MS/MS was performed using an Agilent 1200 nanoflow LC system coupled online with a LTQ ORBITRAP VELOS mass spectrometer. The RPLC column (75 μm i.d.×10 cm) were slurry-packed in-house with 5 μm, 300 Å pore size C-18 stationary phase into fused silica capillaries with a flame pulled tip. The mass spectrometer was operated in a data-dependent mode in which each full MS scan was followed by twenty MS/MS scans wherein the twenty most abundant molecular ions were dynamically selected for collision-induced dissociation (CID) using a normalized collision energy of 35%.

Protein Identification and Quantification

The RPLC-MS/MS data were searched using SEQUEST software through Bioworks interface against a *L. loa* database downloaded from Broad Institute (version 2.2).

Dynamic modifications of methionine oxidation as well as fixed modification of carbamidomethyl cysteine were also included in the database search. Only tryptic peptides with up to two missed cleavage sites meeting a specific SEQUEST scoring criteria [delta correlation ($\Delta C_n$)>=0.1 and charge state dependent cross correlation ($X_{corr}$)≥1.9 for $[M+H]^{1+}$, ≥2.2 for $[M+2H]^{2+}$ and ≥3.5 for $[M+3H]^{3+}$] were considered as legitimate identifications.

Transcriptomics Data mRNA expression levels (putative proteins) of the mf state of *L. loa* were obtained using RNAseq as part of the *L. loa* genome project described in Desjardins et al., *Nat. Genet.,* 45: 495-500 (2013).

Protein/Peptide Selection for Immunoassays

*L. loa* mf proteins identified only in the infected urine (absent in the uninfected urine) were down-selected for immunoassays based on comparison of sequence homologies against human, *L. loa* and other related filarial species (*B. malayi, O. volvulus*, and *W. bancrofti*) or any other relevant nematode for which genome is available.

Proteins that showed no or little homology to non-*Loa* sequences were selected for identification of immunogenic peptides using PROTEAN software (Lasergene Suite). Among these, the 2 peptides that were potentially the most immunogenic and *Loa*-specific (no significant hit to human or other filarial nematodes) per protein were chosen. These peptides were synthesized by the NIAID Peptide Facility as unconjugated free peptides and conjugated to KLH (keyhole limpet hemocyanin), the latter used to produce specific polyclonal antibodies in rabbits.

Generation of Rabbit Polyclonal Antibodies

KLH-conjugated peptides were used to raise polyclonal antisera in rabbits using standard protocols as described in (Suarez-Pantaleon et al., *Anal. Chim. Acta.,* 761: 186-193 (2013)). In addition, polyclonal antisera were raised against a somatic extract of *L. loa* mf using the same standardized protocols. After assessing the reactivity of each of the antisera to its appropriate free peptide by ELISA, the IgG was purified from the sera using Protein A/G (Pierce, Rockford, Ill., USA) columns. These purified IgG antibodies were used as capture antibodies in the luciferase immune-precipitation systems (LIPS) assay for antigen detection.

Fusion Proteins and COS-1 Cells Transfection

Fusion proteins were made for each of the in silico selected proteins by cloning the full-length gene expressing the protein of interest into a FLAG-epitope-tagged mammalian *Renilla reniformis* luciferase (Ruc)-containing expression vector pREN2 (Burbelo et al., *BMC Biotechnol.,* 5: 22 (2005)). Extracts (lysates) containing the light-emitting Ruc-antigen fusions were prepared from 100-$mm^2$ dishes of 48-hours transfected Cos-1 cells as previously described (Burbelo et al., *BMC Biotechnol.,* 5: 22 (2005); Burbelo et al., J. Vis. Exp., doi: 10.3791/1549 (2009)) and frozen until use for LIPS.

LIPS-Based Antibody and Antigen Detection Systems

For evaluating antibody titers, a standard LIPS antibody-based assay was used (Burbelo et al., *J. Clin. Microbiol.,* 46: 2298-2304 (2008); Burbelo et al., *J. Vis. Exp., doi:*10.3791/1549 (2009); Burbelo et al., *Transl. Res.,* 165: 325-335 (2015)). Briefly, 100 μl of the assay master mix (20 mM Tris, pH 7.5, 150 mM NaCl, 5 mM $MgCl_2$, 1% Triton X-100), 1 μl of undiluted plasma/serum, and $2\times10^6$ luminescence units (LU) of the Ruc-antigen fusion protein were added to each well of a 96-well polypropylene plate. This plate was then incubated for 10 minutes at room temperature. Next, 7 μl of a 30% suspension of ULTRALINK protein A/G beads (Pierce, Rockford, Ill., USA) in phosphate-buffered saline (PBS) was added to the bottom of a 96-well filter high throughput-screening plate (Millipore, Bedford, Mass., USA). The 100-μl antigen-antibody reaction mixture from each microtiter well of the 96-well polypropylene plate was then transferred to the well of the filter plate which was further incubated for 10-15 minutes at room temperature. The filter plate containing the mixture was then applied to a vacuum manifold. The retained protein A/G beads were washed with the assay master mix and with PBS (pH=7.4) and the plate was blotted and LU measured in a Berthold LB 960 Centro microplate luminometer, using a coelenterazine substrate mixture (Promega, Madison, Wis., USA).

For quantifying antigens, the original LIPS antibody-testing format was modified for use in a competitive LIPS assay. In competitive LIPS antigen detection, the Renilla luciferase (Ruc) fusion constructs of the antigen of interest are incubated with serum containing unfused antigen. These antigens are then immobilized on agarose beads containing antigen-specific IgG. After washing, the amount of specific antigen present is determined by the inhibition of the Ruc fusion construct by the unfused antigen after adding luciferase substrate.

Having first coupled the purified antigen-specific IgG to ULTRALINK beads (Pierce, Rockford, Ill., USA), 5 μl of a 50% suspension (in PBS) of these beads (specific IgG-ULTRALINK beads) were added to the bottom of a 96-well filter plate. Glycine-treated plasma/sera (Henrard et al., *J. Clin. Microbiol.,* 33: 72-75 (1995)) diluted 1/5 was added to the beads for 30 minutes at room temperature. Then, an optimized number of specific LU of Ruc-antigen fusions was added in each well and incubated for 10 minutes at room temperature. Specific IgG-ULTRALINK beads were washed with the assay master mix, then with PBS. The plate was blotted and LU measured with a Berthold LB 960 Centro microplate luminometer. The percent inhibition was calculated for each sample, and the quantity of specific protein in each sample estimated by using a standard curve designed using known concentrations of each protein in 1/5 diluted human AB serum (FIG. 7).

All samples were run in duplicate. All LU data presented were corrected for background by subtracting LU values of beads incubated with Ruc-antigens but no sera.

Statistical Analysis

Figures and statistical analyses, including specificity and sensitivity calculations (ROC analysis) and correlations (Spearman rank) were performed using Prism 6.0 (GraphPad Software, Inc., San Diego, Calif., USA). Fischer's exact test was used to compare the percent positivity between groups, and the non-parametric Mann-Whitney test were used to estimate difference in antigen amounts between two groups. All differences were considered significant at the $p<0.05$ level.

Example 1

This example demonstrates the identification of *Loa loa* antigens.

Purified *Loa loa* microfilariae (mf) were obtained from one patient. RNA sequences were obtained from the purified *L. loa* mf. The RNA sequences encoded 15,444 putative *L. loa* mf proteins. The bioinformatics of the 15,444 proteins were analyzed by comparison to proteins in general protein databases (Protein Data Bank (PDB) and Swiss-Prot) and specific protein databases (*Caenorhabditis elegans. Wuchereria bancrofti. Brugia malayi* and *Onchocerca volvulus*). Of the 15,444 proteins, 20 were present in mf excretory-secretory (ES) products. These 20 proteins had little to no homology to any of the other proteins in the databases.

Shotgun proteomics using trypsin digestion was performed on the samples shown in Table 1A, followed by liquid chromatography-tandem mass spectrometry (LC-MS/MS) analysis. *L. loa*-specific proteins, mf ES proteins, and/or abundant proteins were identified, as shown in Table 1A. Mass spectrometry analyses of urine from the *L. loa*-infected individual resulted in the identification of spectra matching to 70 *L. loa* proteins, of which 18 proteins were detectable by at least 2 unique peptides and not present in normal uninfected urine (Table 1A and 1B). All of these 18 proteins were identified to be *L. loa* mf proteins. Their corresponding transcript expression (Desjardins et al., *Nat. Genet.*, 45:495-500 (2013)) (FPKM) ranged from 2.07 to 3,841.10. Eight (44.4%) of the 18 *L. loa* urine specific proteins were annotated as "hypothetical" proteins with unknown function (Table 1B).

TABLE 1A

| | Urine | Serum | ES (in vitro culture) |
|---|---|---|---|
| *L. loa*-infected patients | n = 1 | n = 8 | ES products from 20 × $10^6$ mf isolated by apheresis |
| Uninfected control patients | n = 1 | n = 5 | — |
| *L. loa*-specific proteins | m = 18 | m = 170 | — |
| mf ES proteins | — | — | 1,273 |
| abundant proteins | — | — | 204 |

"n" refers to the number of patients
"m" refers to the number of different proteins

TABLE 1B

| Protein ID | Description | Peptide count | MW (kDa) | FKPM | Homology to Human<br>E-value | % Coverage | Homologue? |
|---|---|---|---|---|---|---|---|
| LOAG_00073 | Heat shock protein 90 | 2 | 69.4 | 3841.1 | 0E+00 | 99 | YES |
| LOAG_01395 | WD repeats and SOF1 domain-containing protein | 2 | 51.0 | 101.3 | 5E−174 | 97 | YES |
| LOAG_01611 | Hypothetical protein | 2 | 64.5 | 29.8 | 1E−85 | 74 | YES |
| LOAG_02628 | Low-density lipoprotein receptor repeat class B containing protein | 2 | 196.0 | 33.7 | 4E−129 | 86 | YES |
| LOAG_03988 | Hypothetical protein | 2 | 54.0 | 152.3 | 2E−08 | 92 | YES |
| LOAG_04876 | Peptidase M16 inactive domain-containing protein | 2 | 47.4 | 40.7 | 2E−43 | 93 | YES |
| LOAG_05583 | U4/U6 small nuclear ribonucleoprotein hPrp4 | 2 | 56.6 | 43.4 | 2E−157 | 99 | YES |
| LOAG_05701 | 14-3-3-like protein 2 | 2 | 28.3 | 2392.0 | 1E−147 | 94 | YES |
| LOAG_05915 | Hypothetical protein | 2 | 104.3 | 14.7 | 2E−02 | 33 | NO |
| LOAG_06631 | Troponin | 2 | 171.1 | 8.8 | 1E−05 | 13 | YES |
| LOAG_09325 | Hypothetical protein | 2 | 33.0 | 68.3 | 1E−13 | 27 | YES |
| LOAG_10011 | Hypothetical protein | 2 | 13.6 | 3257.3 | 7E−66 | 98 | YES |
| LOAG_16297 | Hypothetical protein | 2 | 14.3 | 0.4 | 5E−04 | 67 | NO |
| LOAG_17249 | Pyruvate kinase | 2 | 59.0 | 609.7 | 0E+00 | 99 | YES |
| LOAG_17808 | PWWP domain-containing protein | 2 | 69.8 | 13.9 | 9E−04 | 5 | NO |
| LOAG_18456 | Cullin-associated NEDD8-dissociated protein 1 | 2 | 124.1 | 45.5 | 0E+00 | 98 | YES |
| LOAG_18552 | Hypothetical protein | 2 | 106.5 | 2.1 | 1E−03 | 44 | NO |
| LOAG_19057 | Hypothetical protein | 3 | 30.2 | 89.2 | 5E−128 | 77 | YES |

FPKM represents the relative mRNA expression level obtained using RNAseq (Desjardins et al., *Nat. Genet.*, 45: 495-500 (2013)) and MW stands for "molecular weight".

-

The bioinformatics of the *L. loa*-specific proteins identified in Table 1A were analyzed by comparison to proteins in the general and specific protein databases described above in this Example.

Of the 170 *L. loa*-specific proteins identified in serum in Table 1A, 15 were mostly present in the mf ES products and had little or no homology to any of the other proteins in the databases.

Of the 18 *L. loa*-specific proteins identified in urine in Table 1A, three were present in the mf ES products, and four additional proteins had little or no homology to any of the other proteins in the databases. Further details about the four selected urine proteins are provided in Table 2.

TABLE 2

| | Protein Name (SEQ ID NO) | | | |
|---|---|---|---|---|
| | LOAG_05915 (SEQ ID NO: 1) | LOAG_18552 (SEQ ID NO: 15) | LOAG_17808 (SEQ ID NO: 14) | LOAG_16297 (SEQ ID NO: 4) |
| Description | Hypothetical protein (2736 nucleotides (nt)) | Hypothetical protein (2682 nt) | PWWP domain-containing protein (1878 nt) | Hypothetical protein (375 nt) |
| Sequence size (number of amino acid residues) | 911 | 893 | 625 | 124 |

TABLE 2-continued

| | Protein Name (SEQ ID NO) | | | |
|---|---|---|---|---|
| | LOAG_05915 (SEQ ID NO: 1) | LOAG_18552 (SEQ ID NO: 15) | LOAG_17808 (SEQ ID NO: 14) | LOAG_16297 (SEQ ID NO: 4) |
| molecular weight (MW) | 104.378 | 106.549 | 69.931 | 14.258 |
| secretome P | 0.237 | 0.216 | 0.386 | 0.742 |
| FPKM* | 14.65 | 2.07 | 13.87 | 0.37 |
| Predicted helices | 1 | 0 | 0 | 0 |
| Present in the LLMF ES** | yes | yes | yes | no |

*fragments per kilobase of exon per million fragments mapped
***L. loa* microfilariae excretory-secretory products Of the many proteins present in mf ES products, in the serum, in the urine, or in the transcriptome, 20 proteins (SEQ ID NO: 1-20, respectively) were chosen for further study based on their specificity and abundance.

Filtering the data for proteins with little or no sequence homology with human proteins shortlisted four *L. loa* proteins: LOAG_05915 (SEQ ID NO: 1), LOAG_16297 (SEQ ID NO: 4), LOAG_17808 (SEQ ID NO: 14) and LOAG_18552 (SEQ ID NO: 15) (Tables 1B and 2). These four proteins were then assessed for having homologues in the other filariae sequenced to date, *B. malayi, W. bancrofti*, and *O. volvulus*.

Example 2

This example demonstrates the detection of the protein of LOAG_17808 (SEQ ID NO: 14) in the serum of two *L. loa*-infected patients using a capture ELISA assay.

Rabbit anti-microfilariae ES antibody (IgG) was applied to a plate. A sample of serum from a *L. loa*-infected patient was then applied to the plate. Serum from a mouse that had previously been injected with the LOAG_17808 (SEQ ID NO: 14) was then applied to the plate. The concentration of LOAG_17808 (SEQ ID NO: 14) was determined by measuring the optical density (OD). The results are shown in FIG. 1.

As shown in FIG. 1, LOAG_17808 (SEQ ID NO: 14) was detected in the serum of two unrelated *L. loa*-infected patients.

Example 3

This example demonstrates the specificity of antibody responses to LOAG_16297 (SEQ ID NO: 4) and LOAG_17808 (SEQ ID NO: 14) proteins, respectively, in humans.

A LIPS assay was carried out in which Ruc-antigen (LOAG_16297 (SEQ ID NO: 4) or LOAG_17808 (SEQ ID NO: 14) fusion proteins were incubated with sera from *L. loa*-infected patients, uninfected control patients, or patients infected with *Wuchereria bancrofti* (Wb) or *Onchocerca volvulus* (Ov). Light units were measured with a luminometer.

The results are shown in FIGS. 2A-2B. As shown in FIG. 2A, the human antibody response to LOAG_16297 (SEQ ID NO: 4) demonstrated 100% sensitivity and 92% specificity. As shown in FIG. 2B, the human antibody response to LOAG_17808 (SEQ ID NO: 14) demonstrated 100% sensitivity and 96% specificity.

Example 4

This example demonstrates the detection of LOAG_16297 (SEQ ID NO: 4) and LOAG_17808 (SEQ ID NO: 14), respectively, by a competitive LIPS antigen assay.

Rabbit anti-protein IgG antibody coated agarose beads were applied to a plate. Various doses (0.001 to 100 μg/ml) of antigen (LOAG_16297 (SEQ ID NO: 4) or LOAG_17808) were applied to the beads. After 10 minutes, antigen-LIPS lysate was applied. After 10 minutes, the light units were measured.

The results are shown in FIGS. 3A and 3B. As shown in FIGS. 3A and 3B, LOAG_16297 (SEQ ID NO: 4) and LOAG_17808 (SEQ ID NO: 14) were detected by a competitive LIPS antigen assay.

Example 5

This example demonstrates the immunogenicity of the four LOAG_05915 (SEQ ID NO: 1), LOAG_16297 (SEQ ID NO: 4), LOAG_17808 (SEQ ID NO: 14) and LOAG_18552 (SEQ ID NO: 15) *L. loa* proteins.

The immunogenicity of the protein antigens was assessed using hyperimmune rabbit antisera in a standard LIPS assay. As shown in FIG. 5, there was minimal reactivity with the respective pre-bleed sera, and robust reactivity with the hyperimmune sera (and their purified IgG) from two of the four fusion proteins, LOAG_17808 and LOAG_16297. In addition, the LOAG_17808 fusion protein was also recognized by purified IgG antibodies raised against *L. loa* somatic mf antigen (FIG. 5).

To evaluate the reactivity of these proteins in humans, sera/plasma from *L. loa*-infected (patients) and uninfected (control) subjects were used and compared to the reactivity to *L. loa* SXP-1, a previously described *L. loa* antigen (Burbelo et al., J. Clin. Microbiol., 46: 2298-2304 (2008)). As expected, healthy-control samples had very low signals, with a median anti-LOAG_16297, LOAG_17808, and SXP-1 antibody titers of 236 LU, 97 LU, and 746 LU, respectively (FIGS. 6A-6C). For *L. loa*-infected patients, the median value was 6 times higher for LOAG_16297 (1,423 LU), 148 times higher for LOAG_17808 (14,317 LU), and 905 times for SXP-1 (674,990 LU) than the median titers of the uninfected healthy controls. The difference between *L. loa* infected patients and uninfected controls were significant for all tested fusion proteins (P<0.0001). In addition, a ROC analysis shows that the two *L. loa* mf antigens were able to accurately distinguish *Loa*-infected from *Loa*-uninfected individuals: LOAG_16297 with 96.7% sensitivity and 100% specificity, using a threshold of 760 LU (FIG. 6A), and LOAG_17808 with 100% sensitivity and 96.7% specificity, using a threshold of 862 LU (FIG. 6B). By comparison, *L. loa* SXP-1 showed 100% of sensitivity and 100% of specificity using a threshold of 10,785 LU on the same set of 31 patients and 31 controls (FIG. 6C).

Example 6

This example demonstrates the ability to identify LOAG_16297 and LOAG_17808 using a competitive LIPS assay.

The ability to identify LOAG_16297 and LOAG_17808 in an antigen detection system was next tested using a competitive LIPS assay in *L. loa*-, *W. bancrofti*-, *O. volvulus*-infected individuals and uninfected healthy controls. Using pooled human AB serum spiked with increasing concentrations of the appropriate antigen, standard curves were generated. The standard curves allowed the percent inhibition in the competitive LIPS assay to be related to the antigen concentration present in the sera (FIG. 7). These standard curves were then used to quantitate the levels of circulating protein in the serum of *Loa*-infected patients and in the control groups. For LOAG_16297 (FIG. 8A), the geometric mean level of detectible protein in serum/plasma was 17.88 ng/ml in *Loa*-infected subjects, whereas it was negligible in *W. bancrofti*-, *O. volvulus*-infected and in uninfected subjects. Using a cutoff based on a ROC analysis (5 ng/ml), it can be seen that there were measurable antigen levels in 12/26 microfilaremic *Loa*-infected individuals compared to 0/5 amicrofilaremic *Loa*-infected, 0/31 uninfected (P<0.0001), 0/15 *O. volvulus*- (P=0.004) and 1/15 *W. bancrofti*-infected (P=0.03) individuals. For LOAG_17808 (FIG. 8B), the geometric mean level of protein was 36.68 ng/ml in *Loa*-infected, 21.04 ng/ml in *W. bancrofti*-infected. 1.86 ng/ml in *O. volvulus*-infected, and 4.97 ng/ml in uninfected individuals. Again using ROC analysis (with an upper threshold of 39 ng/ml), there were detectible LOAG_17808 levels in 9/26 microfilaremic *Loa*-infected subjects for 0/5 in the amicrofilaremic *Loa*-infected, 0/31 in the uninfected control (P=0.002), 0/15 *O. volvulus*- (P=0.02) and 4/15 in the *W. bancrofti*-infected (P=0.9) groups.

Example 7

This example compares the performance of the LOAG_16297 and LOAG_17808 LIPS to microscopy.

To further assess the performance of the LOAG_16297 and LOAG_17808-based LIPS antigen detection assays, modified competitive LIPS assays were run using plasma from 26 *Loa*-microfilaremic (*Loa*-mf+) subjects with a range of mf counts and from 25 healthy (uninfected) individuals (Table 3). Considering microcopy to be the "gold standard" for *L. loa* mf quantification, the LOAG_16297 antigen LIPS had a sensitivity of 76.9% (95% confidence interval [95% CI]: 56.3% to 91.0%), a specificity of 96.0% (95% CI: 79.6% to 99.9%), a positive predictive value (PPV) of 95.2% (95% CI: 76.2% to 99.9%) and a negative predictive value (NPV) of 80% (95% CI: 61.4% to 92.2%). For the LOAG_17808 competitive LIPS assay, the sensitivity, specificity, PPV and NPV was 80.7 (95% CI: 60.6% to 93.5%), 37.5 (95% CI: 18.8% to 59.4%), 58.3% (95% CI: 40.8% to 74.5%), and 64.3% (95% CI: 35.1% to 87.2%).

TABLE 3

| Assays | Status | Mf+ | Mf− | Sensitivity (95% CI) | Specificity (95% CI) | PPV (95% CI) | NPV (95% CI) |
|---|---|---|---|---|---|---|---|
| LOAG_16297 | Positive | 20 | 1 | 76.9% | 96.0% | 95.2% | 80.0% |
| LIPS | Negative | 6 | 24 | (56.3-91.0) | (79.6-99.9) | (76.2-99.9) | (61.4-92.3) |
| LOAG_17808 | Positive | 21 | 15 | 80.7% | 37.5% | 58.3% | 64.3% |
| LIPS | Negative | 5 | 9 | (60.6-93.5) | (18.8-59.4) | (40.8-74.5) | (35.1-87.2) |

PPV stands for positive predictive value and NPV for negative predictive value. The 95% confidence interval (95% CI) is indicated for each parameter.

Example 8

This example demonstrates the correlation between the amount of LOAG_16297 antigen and the number of microfilariae.

To evaluate if the levels of antigen circulating in the plasma of *Loa*-infected individuals with range of mf counts were correlated with the density of mf, Spearman rank correlation was performed between the plasma concentrations of LOAG_16297 and LOAG_17808 proteins and the corresponding counts of *L. loa* mf as determined by microscopy (FIG. 9A-9B). As can be seen, there was a significant positive correlation for LOAG_16297 (r=0.71; P<0.0001; FIG. 9A) and for LOAG_17808 (r=0.61; P=0.0002; FIG. 9B).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of detecting the presence of *Loa loa* antigens in a biological sample from a subject, the method comprising assaying the biological sample to determine the presence of one or more antigens in the biological sample, each antigen having a different amino acid sequence selected from the group consisting of SEQ ID NOs: 1, 4, 14, and 15, wherein the presence of at least one of the antigens in the biological sample is indicative of the presence of *Loa loa* in the subject.

2. The method according to claim 1, comprising assaying the biological sample to determine the presence of two or more antigens, each antigen having a different amino acid sequence selected from the group consisting of SEQ ID NOs: 1, 4, 14, and 15 in the biological sample, wherein the presence of at least two of the antigens in the biological sample is indicative of the presence of *Loa loa* in the subject.

3. The method according to claim 1, comprising:

(a) contacting the biological sample with one or more specific binding partner(s), each of which specifically binds to a different amino acid sequence selected from the group consisting of SEQ ID NOs: 1, 4, 14, and 15, thereby forming one or more complexes; and (b) detecting the one or more complexes, wherein detection of the one or more complexes is indicative of *Loa loa* in the subject.

4. The method according to claim 3, wherein the specific binding partner is an antibody, or an antigen binding fragment thereof.

5. The method according to claim 3, comprising:

(a) contacting the biological sample with two or more specific binding partner(s), each of which specifically binds to a different amino acid sequence selected from the group consisting of SEQ ID NOs: 1, 4, 14, and 15, thereby forming two or more complexes; and (b) detecting the two or more complexes, wherein detection of the two or more complexes is indicative of *Loa loa* in the subject.

6. The method according to claim 1, comprising:

(a) contacting the biological sample with a first specific binding partner that specifically binds to one of the antigens, thereby forming a first complex;

(b) contacting the first complex with a second specific binding partner that specifically binds to the first complex, thereby forming a second complex; and (c) detecting the second complex, wherein detection of the second complex is indicative of the presence of *Loa loa* in the subject.

7. The method according to claim 6, wherein the first specific binding partner is a first antibody, or an antigen binding fragment thereof, and the second specific binding partner is a second antibody, or an antigen binding fragment thereof.

8. A method of detecting the presence of *Loa loa* in a biological sample from a subject, the method comprising assaying the biological sample to determine the presence of one or more antibodies in the biological sample, each antibody specifically binding to an antigen having a different amino acid sequence selected from the group consisting of SEQ ID NOs: 1, 4, 14, and 15, wherein the presence of at least one of the antibodies in the biological sample is indicative of the presence of *Loa loa* in the subject.

9. The method of claim 8, comprising assaying the biological sample to determine the presence of two or more antibodies in the biological sample, each antibody specifically binding to an antigen having a different amino acid sequence selected from the group consisting of SEQ ID NOs: 1, 4, 14, and 15, wherein the presence of at least two of the antibodies is indicative of the presence of *Loa loa* in the subject.

10. The method according to claim 1, wherein the assaying is carried out by immunoprecipitation, immunonephelometry, radioimmunoassay (RIA), enzyme immunoassay (EIA), fluorescent immunoassay (FIA), luciferase immunoprecipitation system (LIPS), or lateral flow immunochromatographic assay.

11. The method of claim 10, wherein the assaying is carried out by enzyme-linked immunosorbent assay (ELISA).

12. The method of claim 1, wherein the biological sample is a human biological sample.

13. The method of claim 1, wherein the biological sample is whole blood, serum, or plasma.

14. The method of claim 1, wherein the biological sample is urine.

15. The method of claim 1, wherein the biological sample is saliva.

16. A composition comprising an immunologically-stimulatory concentration of at least one isolated or purified antigen, each antigen having a different amino acid sequence selected from the group consisting of SEQ ID NOs: 1, 4, 14, and 15 and a physiologically-acceptable carrier, and further comprising an adjuvant.

17. A method for producing an antibody that specifically binds to an antigen having an amino acid sequence selected from the group consisting of SEQ ID NOs: 1, 4, 14, and 15, the method comprising administering the composition of claim 16 to an animal under conditions sufficient for the animal to develop an immune response to the antigen.

18. The method of claim 17, comprising harvesting serum from the animal after the animal has developed the immune response, wherein the serum comprises the antibody.

19. The method of claim 17, comprising harvesting a splenocyte from the animal after the animal has developed the immune response, fusing the splenocyte with an immortalized cell to form a hybridoma which secretes the antibody into culture medium, culturing the hybridoma, and harvesting the culture medium containing the antibody.

20. A test kit comprising:

(a) one or more antigens, each antigen having a different amino acid sequence selected from the group consisting of SEQ ID NOs: 1, 4, 14, and 15;

(b) one or more substrate(s) onto which (a) is bound or affixed;

(c) one or more reagent(s) for facilitating binding of one or more antibodies to (a); and (d) one or more reagent(s) for detecting the antibody or antibodies specifically bound to (a).

21. The method according to claim 1, wherein each antigen has a different amino acid sequence selected from the group consisting of SEQ ID NOs: 4 and 14.

22. The method according to claim 17, wherein the antigen has an amino acid sequence selected from the group consisting of SEQ ID NOs: 4 and 14.

23. The composition according to claim 16, wherein each antigen has a different amino acid sequence selected from the group consisting of SEQ ID NOs: 4 and 14.

24. The test kit according to claim 20, wherein each antigen has a different amino acid sequence selected from the group consisting of SEQ ID NOs: 4 and 14.

25. The method according to claim 1, wherein the antigen has the amino acid sequence SEQ ID NO: 1.

26. The method according to claim 1, wherein the antigen has the amino acid sequence SEQ ID NO: 4.

27. The method according to claim 1, wherein the antigen has the amino acid sequence SEQ ID NO: 14.

28. The method according to claim 1, wherein the antigen has the amino acid sequence SEQ ID NO: 15.

* * * * *